US008529893B2

(12) United States Patent
Welcher et al.

(10) Patent No.: US 8,529,893 B2
(45) Date of Patent: *Sep. 10, 2013

(54) METHODS FOR TREATING IFN-γ MEDIATED DISEASES USING HUMAN ANTI-IFN-γ NEUTRALIZING ANTIBODIES AS SELECTIVE IFN-GAMMA PATHWAY INHIBITORS

(75) Inventors: Andrew A. Welcher, Ventura, CA (US); Hilary T. Chute, Calabasas, CA (US); Yue-Sheng Li, Thousand Oaks, CA (US); Haichun Huang, Fremont, CA (US)

(73) Assignees: Amgen Inc., Thousand Oaks, CA (US); Medarex, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/476,317

(22) Filed: May 21, 2012

(65) Prior Publication Data
US 2012/0269819 A1    Oct. 25, 2012

Related U.S. Application Data

(60) Division of application No. 12/831,087, filed on Jul. 6, 2010, now Pat. No. 8,202,976, which is a division of application No. 11/962,594, filed on Dec. 21, 2007, now Pat. No. 7,790,859, which is a continuation of application No. 10/684,957, filed on Oct. 14, 2003, now Pat. No. 7,335,743.

(60) Provisional application No. 60/479,241, filed on Jun. 17, 2003, provisional application No. 60/419,057, filed on Oct. 16, 2002.

(51) Int. Cl.
*A61K 39/395* (2006.01)
(52) U.S. Cl.
USPC .................. 424/130.1; 424/133.1; 424/178.1
(58) Field of Classification Search
None
See application file for complete search history.

(56) References Cited

U.S. PATENT DOCUMENTS

| | | | |
|---|---|---|---|
| 4,599,306 A | 7/1986 | Altrock | |
| 4,727,138 A | 2/1988 | Goeddel et al. | |
| 4,897,264 A | 1/1990 | Novick et al. | |
| 4,948,738 A | 8/1990 | Banchereau et al. | |
| 5,451,658 A | 9/1995 | Seelig | |
| 5,582,824 A | 12/1996 | Goeddel et al. | |
| 5,632,988 A | 5/1997 | Ingram et al. | |
| 5,693,761 A | 12/1997 | Queen et al. | |
| 5,763,210 A | 6/1998 | Novick et al. | |
| 5,888,511 A | 3/1999 | Skurkovich et al. | |
| 6,036,956 A | 3/2000 | Jacob et al. | |
| 6,075,181 A | 6/2000 | Kucherlapati et al. | |
| 6,248,516 B1 | 6/2001 | Winter et al. | |
| 6,329,511 B1 | 12/2001 | Vasquez et al. | |
| 6,333,032 B1 | 12/2001 | Skurkovich et al. | |
| 6,346,247 B1 | 2/2002 | Stafford et al. | |
| 6,350,860 B1 | 2/2002 | Buyse et al. | |
| 6,558,661 B1 | 5/2003 | Ashkenazi et al. | |
| 7,335,743 B2 * | 2/2008 | Welcher et al. | 530/388.15 |
| 7,790,859 B2 * | 9/2010 | Welcher et al. | 530/387.3 |
| 8,202,976 B2 * | 6/2012 | Welcher et al. | 536/23.53 |
| 2002/0058033 A1 | 5/2002 | Raisch et al. | |
| 2002/0091240 A1 | 7/2002 | Vasquez et al. | |
| 2003/0056233 A1 | 3/2003 | Ehrhardt et al. | |
| 2003/0059428 A1 | 3/2003 | Skurkovich et al. | |
| 2003/0228310 A1 | 12/2003 | Skurkovich et al. | |
| 2004/0010810 A1 | 1/2004 | Kucherlapati et al. | |
| 2005/0004353 A1 | 1/2005 | Welcher et al. | |

FOREIGN PATENT DOCUMENTS

| | | |
|---|---|---|
| DE | 4213497 A1 | 10/1993 |
| EP | 0528469 A1 | 2/1993 |
| WO | 8807869 A2 | 10/1988 |
| WO | 9102005 A1 | 2/1991 |
| WO | 9206115 A1 | 4/1992 |
| WO | 9737679 A1 | 10/1997 |
| WO | 9909055 A2 | 2/1999 |
| WO | 0071585 A1 | 11/2000 |
| WO | 0154721 A1 | 8/2001 |
| WO | 2004046306 A2 | 6/2004 |

OTHER PUBLICATIONS

Acc: A49047; GI:477471, Mar. 20, 1998.
Acc: AAA18271; GI:483388, May 25, 1994.
Acc: AAR66339, Aug. 4, 1995.
Acc: BAC01578; GI:21669107, Jul. 2, 2002.
Acc: BAC01595; GI:21669141, Jul. 2, 2002.
Acc: BAC01767; GI:21669485, Jul. 2, 2002.
Acc: AAB99113; GI:1499961, Jan. 28, 1998.
Acc: AAM23996; GI:20515725; May 9, 2002.
Acc: C36006; GI:106413, Dec. 16, 1998.
Acc: AAUO2582, Aug. 29, 2001.
Acc: AAG62966, Oct. 1, 2001.
Acc: AAW27555, Jan. 23, 1998.
Acc: AR66339, Aug. 4, 1995.
Acc: AAR22575, May 21, 1992.
Acc: AB063950; GI:21669106, Jul. 2, 2002.
Acc: CAD19912; GI:18041706; EMBL Acc: AJ426222, Jan. 1, 2002.
EMBL Locus Acc: CAC94629; GI:16116903, Nov. 15, 2001. ( EMBL Acc: AJ415729 ).
EMBL Locus Acc: AL591130; GI:13990326, Dec. 19, 2001.
GenBank Acc: BQ709764, GI:21848663, Jul. 11, 2002.
GenBank Acc: BG758749; GI:14069402, May 14, 2001.
GenBank Acc: BF917294; GI:12308765, Jan. 18, 2001.
GenBank Acc: BQ709764; GI:21848663, Jul. 11, 2002.
GenBank Acc: BG758749; GI:14069402, May 14, 2001.
GenBank Acc: BG754240; GI:14064893, May 14, 2001.
GenBank Acc: BM920470; GI:19370849, Mar. 11, 2002.
GenBank Acc: BG755575; GI:14066228, May 14, 2001.

(Continued)

*Primary Examiner* — Yunsoo Kim
(74) *Attorney, Agent, or Firm* — McDonnell Boehnen Hulbert & Berghoff LLP

(57) ABSTRACT

This invention provides antibodies that interact with or bind to human interferon-gamma (IFN-γ) and methods for treating IFN-γ mediated diseases by administering a pharmaceutically effective amount of antibodies to IFN-γ. Methods of detecting the amount of IFN-γ in a sample using antibodies to IFN-γ are also provided.

20 Claims, 15 Drawing Sheets

(56) References Cited

OTHER PUBLICATIONS

GenBank Acc: BF663762; GI:11937657, Dec. 18, 2000.
GenBank Acc: BM008329; GI:16522683, Oct. 29, 2001.
TrEMBL: Q9UL89; GI:74725655, May 1, 2000.
Office Action in U.S. Appl. No. 10/684,957, dated Sep. 26, 2005 (18 pages).
Office Action in U.S. Appl. No. 10/684,957, dated Apr. 17, 2006 (11 pages).
Office Action in U.S. Appl. No. 10/684,957, dated Oct. 11, 2006 (13 pages).
Office Action in U.S. Appl. No. 10/684,957, dated Jun. 15, 2007 (8 pages).
Office Action in U.S. Appl. No. 11/437,602, dated Sep. 2, 2008 (16 pages).
Office Action in U.S. Appl. No. 11/437,602, dated Mar. 23, 2009 (11 pages).
Office Action in U.S. Appl. No. 11/437,602, dated Sep. 23, 2009 (12 pages).
Office Action in U.S. Appl. No. 11/437,602, mailed Mar. 24, 2010 (12 pages).
Office Action in U.S. Appl. No. 11/437,602, mailed Jun. 28, 2011 (12 pages).
Office Action in U.S. Appl. No. 11/437,602, mailed Dec. 29, 2011 (13 pages).
Office Action in U.S. Appl. No. 11/962,594, dated Apr. 9, 2009 (7 pages).
Office Action in U.S. Appl. No. 11/962,594, dated Oct. 22, 2009 (6 pages).
Office Action in U.S. Appl. No. 12/831,087, dated Sep. 7, 2011 (6 pages).
Alkan et al., "An interferon-gamma neutralizing monoclonal antibody but not interferon-gamma delays the induction of rat adjuvant arthritis," Abstract, 1987 ISIR Meeting Nov. 2-6, Washington, DC. p. 804, III-17. (1987).
Amital et al., "Immunomodulation of murine experimental SLE-like disease by interferon-γ," 7 Lupus 445-454 (1998).
Attwood, "Genomics. The Babel of bioinformatics," 290 Science 471-73 (2000).
Bach, "Immunointervention in autoimmune diseases from cellular selectivity to autoantigen specificity," 5(Suppl.A) J. Autoimmune 3-10 (1992).
Balasa et al., "Interferon γ (IFN-γ) Is necessary for the genesis of acetylcholine receptor-induced clinical experimental autoimmune myasthenia gravis in mice," 186(3) J. Exp. Med. 385-91 (1997).
Barbas et al., "Human autoantibody recognition of DNA," 28:92(7) Proc. Nat'l. Acad. Sci. USA 2529-33 (1995).
Beiboer et al., "Guided selection of a pan carcinoma specific antibody reveals similar binding characteristics yet structural divergence between the original murine antibody and its human equivalent," 296(3) J. Mol. Biol. 833-49 (2000).
Billiau, "Gamma-interferon: the match that lights the fire?," 9(2) Immunol. Today 37-40 (1988).
Billiau, "Interferons and Inflammation," 7(5) J. Interferon Res. 559-67 (1987).
Billiau and Dijkmans "Commentary—Interferon-γ: Mechanism of action and therapeutic potential," 40(7) Biochem. Pharmacol. 1433-39 (1990).
Billiau et al., "Enhancement of experimental allergic encephalomyelitis in mice by antibodies against IFN-γ," 140(5) J. Immunol.1506-10 (1988).
Billiau et al., "A role for the interferon system in the pathogenesis of multiple sclerosis?," 1(1) J. Biol. Regul. Homeost. Agents 9-22 (1987).
Boissier et al., "Immunotherapy of collagen-induced arthritis with monoclonal antibody to interferon-γ," Abstract, 56th Annual Scientific Meeting, American College of Rheumatology, Atlanta, GA, Oct. 11-15, p. S99, A186 (1992).
Boissier et al., "Biphasic effect of interferon-γ in murine collagen-induced arthritis," 25(5) Eur. J. Immunol. 1184-90 (1995).

Campell et al., "Essential role for interferon-γ and interleukin-6 in autoimmune insulin-dependent diabetes in NOD/Wehi mice," 87(2) J. Clin. Invest. 739-42 (1991).
Chen et al., "Generation and analysis of random point mutations in an antibody CDR2 sequence: many mutated antibodies lose their ability to bind antigen," 176(3) J. Exp. Med. 855-66 (1992).
Chothia and Lesk, "Canonical structures for the hypervariable regions in immunoglobulins," 196(4) J. Mol. Biol. 901-17 (1987).
Clinical Trials News, Apr. 27, 2007, pp. 1-8.
Cush and Kavanaugh, "Biologic interventions in rheumatoid arthritis," 21(3) Rheum Dis Clin North Am. 797-816 (1995).
Desiderio et al., "A semi-synthetic repertoire of intrinsically stable antibody fragments derived from a single-framework scaffold," 310(3) J. Mol. Biol. 603-15 (2001).
Desmyter et al., "Antigen specificity and high affinity binding provided by one single loop of a camel single-domain antibody," 276(28) The J. of Biol. Chem. 26285-90 (2001).
Dijkmans and Billiau, "Interferon γ: a master key in the immune system," 1(2) Curr. Opin. Immunol. 269-74 (1988).
Ditzel et al., "Determinants of polyreactivity in a large panel of recombinant human antibodies from HIV-1 infection," 157(2) J. Immunol. 739-49 (1996).
Duong et al., "Effect of anti-interferon-γ and anti-interleukin-2 monoclonal antibody treatment on the development of actively and passively induced experimental allergic encephalomyelitis in the SJL/J mouse," 36(2-3) J. Neuroimmunol. 105-15 (1992).
Espejo et al., "Treatment with anti-interferon-γ monoclonal antibodies modifies experimental autoimmune encephalomyelitis in interferon-γ receptor knockout mice," 172(2) Exp. Neurol. 460-68 (2001).
Ferber et al., "Mice with a disrupted IFN-γ gene are susceptible to the induction of experimental autoimmune encephalomyelitis (EAE)1", 156(1) J. Immunol. 5-7 (1996).
Fiorentini et al., "A partially humanized monoclonal antibody to human IFN-γ inhibits cytokine effects both in vitro and in vivo," 55(3) Scand. J. Immunol. 284-92 (2002).
Froyen and Billiau, "Potential therapeutic use of antibodies directed towards HuIFN-γ," 10(1) Biotherapy 49-57 (1997).
William E. Paul, Fundamental Immunology, 242 (3rd Ed. 1993).
Haas C et al., "IFN-γ receptor deletion prevents autoantibody production and glomerulonephritis in lupus-prone (NZB x NSW)Fi Mice," J. Immunol. 1998; 160:3713-3718.
Hartung et al., "The role of interferon-gamma in the pathogenesis of experimental autoimmune disease of the peripheral nervous system," 27(3) Ann. Neurol. 247-57 (1990).
Hasemann & Capra, "Immunoglobulins: Structure and Function," Fundamental Immunology, 288-92 (William E. Paul, ed., 3rd edition, 1993).
Heremans and Billiau, "The potential role of interferons and interferon antagonists in inflammatory disease," 38(6) Drugs 957-72 (1989).
Heremans et al., "Clinical potential of monoclonal antibodies against gamma interferon," 71 Develop. Biol. Standard 113-19 (1990).
Heremans et al., "Interferon γ, a mediator of lethal lipopolysaccharide-induced shwartzman-like shock reactions in mice," 171(6) J. Exp. Med. 1853-69 (1990).
Inagaki et al., "Interferon-γ-induced apoptosis and activation of THP-1 macrophages," 71(21) Life Sci. 2499-508 (2002).
IFN gamma Abs PubMed Abst.txt, 3 pages (Nov. 27, 2006).
Ishida et al., "A pivotal involvement of IFN-γ in the pathogenesis of acetaminophen-induced acute liver injury," 16(10) FASEB J. 1227-36 (2002).
Jacob et al., "In vivo treatment of (NZB x NZW)F1 lupus-like nephritis with monoclonal antibody to γ-interferon," 166 (3) J. Exp. Med. 798-803 (1987).
Jacob et al., "Heterogeneous effects of IFN-γ in adjuvant arthritis," 142(5) J. Immunol. 1500-05 (1989).
Janeway et al., Immunobiology, 110-12 (6th Ed., 2004).
Jones et al., "Replacing the complementarity-determining regions in a human antibody with those from a mouse," 321 (6069) Nature 522-5 (1986).
Kabat et al., Sequences of Proteins of Immunological Interest, NIH Publication No. 91-3242 (5th Ed. 1991).

Kageyama et al., "Reduced susceptibility to collagen-induced arthritis in mice deficient in IFN-γ receptor," 161(3) J. Immunol.1542-8 (1998).

Klimka et al., "Human anti-CD30 recombinant antibodies by guided phage antibody selection using cell panning," 83 (2) Br. J. Cancer 252-60 (2000).

Landolfi et al., "The integrity of the ball-and-socket joint between V and C domains is essential for complete activity of a humanized antibody," 166(3) The J. of Immunol. 1748-64 (2001).

Landolfo et al., "Inhibition of interferon-gamma may suppress allograft reactivity by T lymphocytes in vitro and in vivo," 229(4709) Science 176-9 (1995).

Lukina et al., "Double blind trial of effectiveness of antibodies to interferon-gamma and tumor necrosis factor-alpha in rheumatoid arthritis," 73(5) Ter. Arkh. 12-5 (2001).

Lukina et al., "New approaches to biological immunomodulation therapy of rheumatoid arthritis: Neutralization of basic cytokines," 70(5) Ter. Arkh. 32-7 (1998).

MacDoughall and Cooper, "Erythropoietin resistance: the role of inflammation and pro-inflammatory cytokines," 17(Suppl 11) Nephrol. Dial Transplant 39-43 (2002).

Merck Manual Medical Information; pp. 1018-1019, 1999.

Metzler et al., "Solution structure of human CTLA-4 and delineation of a CD80/CD86 binding site conserved in CD28," 4(7) Nature Struct. Biol. 527-31 (1997).

Mizuhara et al., "Critical involvement of interferon gamma in the pathogenesis of T-cell activation—associated hepatitis and regulatory mechanisms of interleukin-6 for the manifestations of hepatitis," 23(6) Hepatology 1608-15 (1996).

Nagano et al., "Coronary arteriosclerosis after T-cell-mediated injury in transplanted mouse hearts," 152(5) Am. J. Pathol. 1187-97 (1998).

Nakajima et al., "The effect of treatment with interferon-gamma on type II collagen-induced arthritis," 81(3) Clin. Exp. Immunol. 441-5 (1990).

Nicoletti et al., "Murine concanavalin A-induced hepatitis is presented by interleukin 12 (IL-12) antibody and exacerbated by exogenous IL-12 through an interferon-γ-dependent mechanism," 32(4Pt.1) Hepatology 728-33 (2000).

Nicoletti et al., "Immunoglobulin treatment reduces atherosclerosis in apo E knockout mice," 102(5) J. Clin. Invest. 910-8 (1998).

Nicoletti et al., "Prevention of spontaneous autoimmune diabetes in diabetes-prone BB rats by prophylactic treatment with antirat interferon-γ antibody," 138(1) Endocrinology 281-8 (1997).

Ozmen et al., "Experimental therapy of systemic lupus erythematosus: the treatment of NZB/W mice with mouse soluble interferon-γ receptor inhibits the onset of glomerulonephritis," 25(1) Eur. J. Immunol. 6-12 (1995).

Panitch et al., "Exacerbations of multiple sclerosis in patients treated with gamma interferon," 1(8538) Lancet 893-5 (1987).

Portolano et al., "Lack of promiscuity in autoantigen-specific H and L chain combinations as revealed by human H and L chain "roulette"," 150(3) J. Immunol. 880-7 (1993).

Rader et al., "A phage display approach for rapid antibody humanization: designed combinatorial V gene libraries," 95(15) Proc. Natl. Acad. Sci. USA 8910-15 (1998).

Repik et al., "The promise of CCR5 antagonists as new therapies for HIV-1," 8(2) Current Opin. Investig. Drugs 130-9 (2007).

Richards et al., "Interferon-γ is required for lupus nephritis in mice treated with the hydrocarbon oil pristane," 60(6) Kidney Int'l. 2173-80 (2001).

Rudikoff et al., "Single amino acid substitution altering antigen-binding specificity," 79(6) Proc. Nat. Acad. Sciences USA 1979-83 (1982).

Russell et al., "Coronary atherosclerosis in transplanted mouse hearts. III. Effects of recipient treatment with a monoclonal antibody to interferon-gamma," 57(9) Transplantation 1367-71 (1994).

Sandborn and Targan, "Biologic therapy of inflammatory bowel disease," 122(6) Gastroenterology 1592-1608 (2002).

Schier et al., "Identification of functional and structural amino-acid residues by parsimonious mutagenesis," 169(2) Gene 147-55 (1996).

Schier et al., "Isolation of picomolar affinity anti-c-erbB-2 single chain Fv by molecular evolution of the complementarity determining regions in the center of the antibody binding site," 263(4) J. Mol. Biol. 551-67 (1996).

Seery, "IFN-γ transgenic mice: clues to the pathogenesis of systemic lupus erythematosus?," 2(6) Arthritis. Res. 437-40 (2000).

Sigidin et al., "Randomized, double-blind trial of anti-interferon-γ antibodies in rheumatoid arthritis," 30(4) Scan. J. Rheumatol. 203-7 (2001).

Skolnick and Fetrow, "From genes to protein structure and function: novel applications of computational approaches in the genomic era," 18(1) Trends in Biotech 34-9 (2000).

Skurkovich and Skurkovich, "Anti-interferon-γ antibodies in the treatment of autoimmune diseases," 5(1) Current Opinion in Mol Ther. 52-7 (2003).

Skurkovich et al., "Randomized study of antibodies to IFN-gamma and TNF-alpha in secondary progressive multiple sclerosis," 7(5) Multiple Sclerosis 277-84 (2001).

Skurkovich SV et al., "Successful First-Time Use of Antibodies to Interferon-γ Alone and combined with Antibodies to Tumor Necrosis Factor-a to Treat Rheutmatic Diseases (Rheumatoid Arthritis, Systemic Lupus Erythematosus, Psoriatic Arthritis, Behcet's Syndrome)," Int J Immunotherapy 1998; XIV(1):23-32.

Skurkovich and Eremkina, "The probable role of interferon in allergy," 35(6) Annals Allergy 356-60 (1975).

Skurkovich et al., "A unifying model of the immunoregulatory role of the interferon system: can interferon produce disease in humans," 43(3) Clin. Immunol. Immunopathol. 362-73 (1987).

Skurkovich et al., "Lymphocytes' cytotoxicity towards cells of human lymphoblastoid lines in patients with rheumatoid arthritis and systemic lupus erythematosus," 39(5) Annals Allergy 344-50 (1977).

Skurkovich et al., "The possible participation of intereferon inhibitor in the formation of the remission in autoimmune diseases and allergy (hypersensitivity of immediate type)," 7(9) Med.Hypotheses 1189-91 (1981).

Skurkovich et al., "A disturbance of interferon synthesis with the hyperproduction of unusual kinds of interferon can trigger autoimmune disease and play a pathogenetic role in AIDS: The removal of these interferons can be therapeutic," 42(1) Med. Hypotheses 27-35 (1994).

Tang et al., "The effects of a monoclonal antibody to interferon-γ on experimental autoimmune thyroiditis (EAT): prevention of disease and decrease of EAT-specific T cells," 23(1) Eur. J. Immunol. 275-78 (1993).

Thakur and Landolfi, "A potent neutralizing monoclonal antibody can discriminate amongst IFN γ from various primates with greater specificity than can the human IFNγ receptor complex," 36(15-16) Mol. Immunol. 1107-15 (1999).

Vantrappen et al., "Treatment of Crohn's disease with interferon. A preliminary clinical trial," 35(4) Acta. Clin. Belg. 238-42 (1980).

Verhoeyen et al., "Reshaping human antibodies: grafting an antilysozyme activity," 239(4847) Science 1534-6 (1988).

Whitman et al., "IFN-γ deficiency exerts gender-specific effects on atherogenesis in apolipoprotein E-/- mice," 22(6) J. Interferon Cytokine Res. 661-670 (2002).

Wiesenberg et al., "Suppression and augmentation of rat adjuvant arthritis with monoclonal anti-interferon-gamma antibody," 78(2) Clin. Exp. Immunol. 245-9 (1989).

Williams et al., "Increased limb involvement in murine collagen-induced arthritis following treatment with anti-interferon-gamma," 92(2) Clin. Exp. Immunol. 323-7 (1993).

Wu et al., "Modulation of MMP-2 (gelatinase A) and MMP-9 (gelantinase B) by interferon-γ in a human salivary gland cell line," 171(2) J. Cell Physic. 117-24 (1997).

Yamamoto et al., "Characterization of mouse monoclonal antibodies to human interferon-gamma," 32(4) Microbiol. Immunol. 339-50 (1988).

Yang et al., "CDR walking mutagenesis for the affinity maturation of a potent human anti-HIV-1 antibody into the picomolar range," 254(3) J. Mol. Biol. 392-403 (1995).

Xu and Davis, "Diversity in the CDR3 region of VH is sufficient for most antibody specificities," 13(1) Immunity 37-45 (2000).

Zhou et al., "Hypercholesterolemia is associated with a T helper (Th) 1/Th2 switch of the autoimmune response in atherosclerotic apo E-knockout mice," 101(8) J. Clin. Invest. 1717-25 (1998).
Acc: AL132795; GI:7159766, Aug. 1, 2000.
Acc: AL160175; GI:8217646, Jul. 5, 2002.
Acc: G47578; GI:4494186, Mar. 23, 1999.
Acc: G30544; GI:1594095, Oct. 5, 1996.
Acc: 1ID2_A; GI:14278664, Apr. 3, 2001.
Acc: AU048895; GI:6722066, Jan. 20, 2000.
Acc: AAU14464; GI:51949179, Oct. 24, 2001.

* cited by examiner

FIG. 1A

Heavy Chain IgG1 Constant Region

```
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagaa agttgagccc   300
aaatcttgtg acaaaactca cacatgccca ccgtgccag cacctgaact cctggggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggatgag   720
ctgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctat agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa                                     990
```

FIG. 1B

```
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330
```

FIG. 2A

Kappa Chain Constant Region

```
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                             321
```

FIG. 2B

```
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107
```

FIG. 3A

1119 Heavy Chain Variable Region

```
gaggtgcagc tggtacagtc tggagcagag gtgaaaaagc ccggggagtc tctgaagatc    60
tcctgtaagg gttctggata caactttacc agctactgga tcggctgggt gcgccagatg   120
cccgggaaag gcctggagtt gatggggatc atctatcctg gtgactctga taccagatac   180
agcccgtcct tccaaggcca ggtcaccatc tcagccgaca gtccatcag caccgcctac    240
ctgcagtgga gcagcctgaa ggcctcggac accgccatgt attactgtgg ttcggggagc   300
tacttttact tcgatctctg gggccgtggc accctggtca ccgtctctag t            351
```

FIG. 3B

```
EVQLVQSGAE VKKPGESLKI SCKGSGYNFT SYWIGWVRQM PGKGLELMGI IYPGDSDTRY    60
SPSFQGQVTI SADKSISTAY LQWSSLKASD TAMYYCGSGS YFYFDLWGRG TLVTVSS     117
```

FIG. 4A

1119 Kappa Chain Variable Region

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatatat ggtgcatcca gcagggccac tggcatccca     180
gacaggttca gtggcagtgg gtctgggaca gacttcactc tcaccatcag cagactggag     240
cctgaagatt ttgcagtgta ttactgtcag cggtctggtg gctcatcatt cactttcggc     300
cctgggacca aagtggatat caaa                                            324
```

FIG. 4B

```
EIVLTQSPGT LSLSPGERAT LSCRASQSVS SSYLAWYQQK PGQAPRLLIY GASSRATGIP      60
DRFSGSGSGT DFTLTISRLE PEDFAVYYCQ RSGGSSFTFG PGTKVDIK                 108
```

FIG. 5A

1118 Heavy Chain Variable Region

```
gaggtgcagc tggtgcagtc tggagcagag gtgaaaaagc ccggggagtc tctgaagatc     60
tcctgtaagg gttctggata cagctttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca agtccatcag caccgcctac    240
ctgcagtgga gcagcctgaa ggcctcggac accgccatgt attactgtgg ttcggggagc    300
tactggtact tcgatctctg ggccgtggc accctggtca ccgtctctag t             351
```

FIG. 5B

```
EVQLVQSGAE VKKPGESLKI SCKGSGYSFT SYWIGWVRQM PGKGLEWMGI IYPGDSDTRY     60
SPSFQGQVTI SADKSISTAY LQWSSLKASD TAMYYCGSGS YWYFDLWGRG TLVTVSS      117
```

FIG. 5C

1118* Heavy Chain Variable Region

```
EVQLVQSGAE VKKPGESLKI SCKGSGYSFT SYWIGWVRQM PGKGLEWMGI IYPGDSDTRY     60
SPSFQGQVTI SADKSISTAY LQWSSLKASD TAMYYCGSGS YWYFDLRGRG TLVTVSS      117
```

FIG. 5D

1118* Heavy Chain Variable Region

```
gaggtgcagc tggtgcagtc tggagcagag gtgaaaaagc ccggggagtc tctgaagatc     60
tcctgtaagg gttctggata cagctttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca agtccatcag caccgcctac    240
ctgcagtgga gcagcctgaa ggcctcggac accgccatgt attactgtgg ttcggggagc    300
tactggtact tcgatctccg gggccgtggc accctggtca ccgtctctag t             351
```

FIG. 6A

1118 Kappa Chain Variable Region

```
gaaattgtgt tgacgcagtc tccaggcacc ctgtctttgt ctccagggga aagagccacc    60
ctctcctgca gggccagtca gagtgttagc agcagctcct tagcctggta ccagcagaaa   120
cctggccagg ctcccaggct cctcatatat ggtgcatcca gcagggccac tggcatccca   180
gacaggttca gtggcagtgg gtctgggaca gacttcactc tcaccatcag cagactggag   240
cctgaagatt ttgcagtgta ttactgtcag cggtctggtg gctcatcatt cactttcggc   300
cctgggacca aagtggatat caaa                                          324
```

FIG. 6B

```
EIVLTQSPGT LSLSPGERAT LSCRASQSVS SSSLAWYQQK PGQAPRLLIY GASSRATGIP    60
DRFSGSGSGT DFTLTISRLE PEDFAVYYCQ RSGGSSFTFG PGTKVDIK                108
```

FIG. 7A

1121 Heavy Chain Variable Region

```
gaggtgcagc tggtgcagtc tggagcagag gtgaaaaagc ccggggagtc tctgaagatc    60
tcctgtaagg gttctggata caactttacc agctactgga tcggctgggt gcgccagatg   120
cccgggaaag gcctggagtt gatggggatc atctatcctg gtgactctga taccagatac   180
agcccgtcct tccaaggcca ggtcaccatc tcagccgaca agtccatcag caccgcctac   240
ctgcagtgga gcagcctgaa ggcctcggac accgccatgt attactgtgg ttcggggagc   300
tactggtact tcgatctctg gggccgtggc accctggtca ccgtctctag t            351
```

FIG. 7B

```
EVQLVQSGAE VKKPGESLKI SCKGSGYNFT SYWIGWVRQM PGKGLELMGI IYPGDSDTRY    60
SPSFQGQVTI SADKSISTAY LQWSSLKASD TAMYYCGSGS YWYFDLWGRG TLVTVSS     117
```

FIG. 8A

1121 Kappa Chain Variable Region

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatatat ggtgcatcca gcagggccac tggcatccca   180
gacaggttca gtggcagtgg gtctgggaca gacttcactc tcaccatcag cagactggag   240
cctgaagatt ttgcagtgta ttactgtcag cggtctggtg gctcatcatt cactttcggc   300
cctgggacca aagtggatat caaa                                          324
```

FIG. 8B

```
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ RSGGSSFTFG PGTKVDIK               108
```

FIG. 8C

1121* Kappa Chain Variable Region

```
EIVLTQSPGT LSLSPGERAT LSCRASQSII SSYLAWYQQK PGQTPRLLIY GVSSRATGIP    60
DRFSGSGSGT DFTLTITRLE PEDFAVYYCQ QYGNSFMYTF GQGTKLEIK               109
```

FIG. 8D

1121* Kappa Chain Variable Region

```
gaaattgtgt tgacgcagtc tccaggcacc ctgtctttgt ctccagggga aagagccacc    60
ctctcctgca gggccagtca gagtattatc agcagctact tagcctggta ccagcagaaa   120
cctggccaga ctcccaggct cctcatctat ggtgtatcca gcagggccac tggcatccca   180
gacaggttca gtggcagtgg gtctgggaca gacttcactc tcaccatcac cagactggag   240
cctgaagatt ttgcagtgta ttactgtcag cagtatggta actcatttat gtacactttt   300
ggccagggga ccaagctgga gatcaaa                                       327
```

A549 Assay

THP1 assay

FIG. 12

```
                                                                                                    CDR1
1119   MGSTAILALL LAVLQGVCAE VQLVQSGAEV KKPGESLKIS CKGSGYNFTS YWIGWVRQMP    60
1118   MGSTAILALL LAVLQGVCAE VQLVQSGAEV KKPGESLKIS CKGSGYSFTS YWIGWVRQMP    60
1118*  MGSTAILALL LAVLQGVCAE VQLVQSGAEV KKPGESLKIS CKGSGYSFTS YWIGWVRQMP    60
1121   MGSTAILALL LAVLQGVCAE VQLVQSGAEV KKPGESLKIS CKGSGYNFTS YWIGWVRQMP    60

CDR3
1119   GKGLELMGII YPGDSDTRYS PSFQGQVTIS ADKSISTAYL QWSSLKASDT AMYYCGSGSY   120
1118   GKGLEWMGII YPGDSDTRYS PSFQGQVTIS ADKSISTAYL QWSSLKASDT AMYYCGSGSY   120
1118*  GKGLEWMGII YPGDSDTRYS PSFQGQVTIS ADKSISTAYL QWSSLKASDT AMYYCGSGSY   120
1121   GKGLELMGII YPGDSDTRYS PSFQGQVTIS ADKSISTAYL QWSSLKASDT AMYYCGSGSY   120
                   CDR2

1119   FYFDLWGRGT LVTVSSASTK GPASVFPLAP SSKSTSGGTA ALGCLVKDYP EPVTVSWNSG   180
1118   WYFDLWGRGT LVTVSSASTK GPASVFPLAP SSKSTSGGTA ALGCLVKDYP EPVTVSWNSG   180
1118*  WYFDLRGRGT LVTVSSASTK GPASVFPLAP SSKSTSGGTA ALGCLVKDYP EPVTVSWNSG   180
1121   WYFDLWGRGT LVTVSSASTK GPASVFPLAP SSKSTSGGTA ALGCLVKDYP EPVTVSWNSG   180
```

FIG. 13

```
                                                                       CDR1
1119   METPAQLLFL LLLWLPDTTG EIVLTQSPGT LSLSPGERAT LSCRASQSVS SSYLAWYQQK   60
1118   METPAQLLFL LLLWLPDTTG EIVLTQSPGT LSLSPGERAT LSCRASQSVS SSSLAWYQQK   60
1121   METPAQLLFL LLLWLPDTTG EIVLTQSPGT LSLSPGERAT LSCRASQSVS SSYLAWYQQK   60
1121*  METPAQLLFL LLLWLPDTTG EIVLTQSPGT LSLSPGERAT LSCRASQSIS SSYLAWYQQK   60

CDR2                                              CDR3
1119   PGQAPRLLIY GASSRATGIP DRFSGSGSGT DFTLTISRLE PEDFAVYYCQ RSG-GSSFTFG  120
1118   PGQAPRLLIY GASSRATGIP DRFSGSGSGT DFTLTISRLE PEDFAVYYCQ RSG-GSSFTFG  120
1121   PGQAPRLLIY GASSRATGIP DRFSGSGSGT DFTLTISRLE PEDFAVYYCQ RSG-GSSFTFG  120
1121*  PGQTPRLLIY GVSSRATGIP DRFSGSGSGT DFTLTITRLE PEDFAVYYCQ QYGNSFMYTFG  121

1119   PGTKVDIKRT VAAPSVFIFP PSDEQLKSGT ASVVCLLNNF YPREAKVQWK VDNALQSGNS  180
1118   PGTKVDIKRT VAAPSVFIFP PSDEQLKSGT ASVVCLLNNF YPREAKVQWK VDNALQSGNS  180
1121   PGTKVDIKRT VAAPSVFIFP PSDEQLKSGT ASVVCLLNNF YPREAKVQWK VDNALQSGNS  180
1121*  QGTKLEIKRT VAAPSVFIFP PSDEQLKSGT ASVVCLLNNF YPREAKVQWK VDNALQSGNS  181

1119   QESVT  185
1118   QESVT  185
1121   QESVT  185
1121*  QESVT  186
```

METHODS FOR TREATING IFN-γ MEDIATED DISEASES USING HUMAN ANTI-IFN-γ NEUTRALIZING ANTIBODIES AS SELECTIVE IFN-GAMMA PATHWAY INHIBITORS

CROSS REFERENCE TO RELATED APPLICATION

This application is a division of U.S. application Ser. No. 12/831,087, filed Jul. 6, 2010, now U.S. Pat. No. 8,202,976, which is a division and claims the benefit of U.S. application Ser. No. 11/962,594, filed Dec. 21, 2007, now U.S. Pat. No. 7,790,859, which is a continuation and claims the benefit of the filing date of U.S. application Ser. No. 10/684,957, filed Oct. 14, 2003, now U.S. Pat. No. 7,335,743, which claims the benefit under 35 U.S.C. §119(e) of U.S. Provisional Application No. 60/419,057, filed Oct. 16, 2002, and of U.S. Provisional Application No. 60/479,241, filed Jun. 17, 2003, the disclosures of which are incorporated by reference in their entirety.

TECHNICAL FIELD OF THE INVENTION

The invention relates to human monoclonal antibodies that bind interferon gamma (IFN-γ). Compositions and methods for treating diseases mediated by IFN-γ are also described.

BACKGROUND OF THE INVENTION

Interferons (IFNs) were originally named for their ability to interfere with viral infection of host cells (Isaacs and Lindenman, 1957, *Proc. R. Soc.* 147:28-267). Since their discovery, a number of members of the interferon family have been identified with various biological roles in addition to antiviral defense, including cell growth and cell immunity. Interferon types IFN-α, IFN-β, IFN-ω, and IFN-τ are type I interferons and bind the type I IFN receptor, while IFN-γ is a type II interferon and binds the type II IFN receptor (Pfeffer et al., 1998, *Cancer Res.* 58:2489-2499).

IFN-γ signaling depends on at least five distinct proteins: IFNGR1 and IFNGR2 (subunits of the IFN-γ receptor), Jak1, Jak2 and the transcription factor STAT1 (Schindler and Darnell, 1995, *Annu. Rev. Biochem.* 64:621-651; Bach et al., 1997, *Annu. Rev. Immunol.* 15:563-591). IFN-γ receptors are found on most cell types, except mature erythrocytes (Farrar and Schreiber, 1993, *Annu. Rev. Immunol.* 11:571-611). Jak1, Jak2, and STAT1 proteins mediate IFN-γ signaling.

IFN-γ regulates a variety of biological functions, such as antiviral responses, cell growth, immune response, and tumor suppression, and IFN-γ may mediate a variety of human diseases. Thus, there is a need in the art for agents that can modulate the biological activity of IFN-γ.

SUMMARY OF THE INVENTION

The invention provides monoclonal antibodies that bind to interferon-γ (IFNγ) and polynucleotides that encode them. The antibodies may inhibit or modulate at least one of the biological activities of IFN-γ and can be useful for ameliorating the effects of IFN-γ mediated diseases. Also provided by the invention are hybridoma cells that produce and may secrete into cell culture media the monoclonal antibodies of the invention. The antibodies of the invention can be useful for treating diseases mediated by IFN-γ.

In certain aspects, the invention provides antibodies, optionally monoclonal antibodies and/or human antibodies, which can comprise a heavy chain and a light chain, wherein the heavy chain comprises an amino acid sequence as set forth in SEQ ID NO: 2 or an antigen-binding or an immunologically functional immunoglobulin fragment thereof.

In certain aspects, the invention provides antibodies, optionally monoclonal antibodies, which may be human antibodies, comprising a heavy chain and a light chain, wherein the heavy chain comprises an IgG1, IgG2, or an IgG4 heavy chain constant region. In some embodiments, an antibody of the invention comprises an amino acid sequence of the IgG1 heavy chain constant region as set forth in SEQ ID NO: 2 or an antigen-binding or an immunologically functional immunoglobulin fragment thereof.

In certain aspects, antibodies of the invention comprise a heavy chain and a light chain, wherein the variable region of the heavy chain comprises an amino acid sequence as set forth in any of SEQ ID NO: 6, SEQ ID NO: 10, SEQ ID NO: 14, or SEQ ID NO: 30, or an antigen-binding or an immunologically functional immunoglobulin fragment thereof. In other aspects, the light chain variable region comprises an amino acid sequence as set forth in any of SEQ ID NO: 8, SEQ ID NO: 12, SEQ ID NO: 16, or SEQ ID NO: 31, or an antigen-binding or an immunologically functional immunoglobulin fragment thereof. In additional aspects, the heavy chain comprises an amino acid sequence as set forth in any of SEQ ID NO: 17, SEQ ID NO: 19, SEQ ID NO: 21, or SEQ ID NO: 32, or an antigen-binding or an immunologically functional immunoglobulin fragment thereof. In still further aspects, the light chain comprises an amino acid sequence as set forth in any of SEQ ID NO: 18, SEQ ID NO: 20, SEQ ID NO: 22, or SEQ ID NO: 33, or an antigen-binding or an immunologically functional immunoglobulin fragment thereof.

The invention also provides antibodies that bind specifically to IFN-γ, wherein the heavy chain comprises a heavy chain variable region comprising an amino acid sequence as set forth in SEQ ID NO: 6, or an antigen-binding or an immunologically functional immunoglobulin fragment thereof, and the light chain comprises a light chain variable region comprising an amino acid sequence as set forth in SEQ ID NO: 8, or an antigen-binding or an immunologically functional immunoglobulin fragment thereof.

In certain aspects, the invention also provides antibodies and immunologically functional immunoglobulin fragments thereof that can bind specifically to and/or inhibit or modulate the biological activity of IFN-γ, comprising a heavy chain and a light chain, wherein the heavy chain comprises a heavy chain variable region, and wherein the heavy chain variable region comprises a sequence that has at least 80%, 85%, 90%, 91%, 92%, 93%, 94%, 95%, 96%, 97%, 98%, or about 99% identity to the amino acid sequence as set forth in SEQ ID NO: 6, and wherein the light chain comprises a light chain variable region, and wherein the light chain variable region comprises a sequence that has at least 80%, 85%, 90%, 91%, 92%, 93%, 94%, 95%, 96%, 97%, 98%, or about 99% identity to the amino acid sequence as set forth in SEQ ID NO: 8, wherein the antibody interacts with IFN-γ.

The invention further provides antibodies that can inhibit or modulate the biological activity of and/or specifically bind to IFN-γ, wherein the heavy chain comprises a heavy chain variable region comprising an amino acid sequence as set forth in SEQ ID NO: 10, or an antigen-binding or an immunologically functional immunoglobulin fragment thereof, and the light chain comprises a light chain variable region comprising an amino acid sequence as set forth in SEQ ID NO: 12, or an antigen-binding or an immunologically functional immunoglobulin fragment thereof.

In certain aspects, the invention provides antibodies, which can inhibit or modulate the biological activity of and/or specifically bind to IFN-γ, comprising a heavy chain and a light chain, wherein the heavy chain comprises a heavy chain variable region, and wherein the heavy chain variable region comprises a sequence that has at least 80%, 85%, 90%, 91%, 92%, 93%, 94%, 95%, 96%, 97%, 98%, or about 99% identity to the amino acid sequence as set forth in SEQ ID NO: 10, and wherein the light chain comprises a light chain variable region, and wherein the light chain variable region comprises a sequence that has at least 80%, 85%, 90%, 91%, 92%, 93%, 94%, 95%, 96%, 97%, 98%, or about 99% identity to the amino acid sequence as set forth in SEQ ID NO: 12, wherein the antibody interacts with IFN-γ.

The invention further provides antibodies that can inhibit or modulate the biological activity of and/or specifically bind to IFN-γ, wherein the heavy chain comprises a heavy chain variable region comprising an amino acid sequence as set forth in SEQ ID NO: 30, or an antigen-binding or an immunologically functional immunoglobulin fragment thereof, and the light chain comprises a light chain variable region comprising an amino acid sequence as set forth in SEQ ID NO: 12, or an antigen-binding or an immunologically functional immunoglobulin fragment thereof.

In certain aspects, the invention provides antibodies, which can inhibit or modulate the biological activity of and/or specifically bind to IFN-γ, comprising a heavy chain and a light chain, wherein the heavy chain comprises a heavy chain variable region, and wherein the heavy chain variable region comprises a sequence that has at least 80%, 85%, 90%, 91%, 92%, 93%, 94%, 95%, 96%, 97%, 98%, or about 99% identity to the amino acid sequence as set forth in any of SEQ ID NO: 30, and wherein the light chain comprises a light chain variable region, and wherein the light chain variable region comprises a sequence that has at least 80%, 85%, 90%, 91%, 92%, 93%, 94%, 95%, 96%, 97%, 98%, or about 99% identity to the amino acid sequence as set forth in SEQ ID NO: 12, wherein the antibody interacts with IFN-γ.

The invention also provides antibodies that can inhibit or modulate the biological activity of and/or bind specifically to IFN-γ, wherein the heavy chain comprises a heavy chain variable region comprising an amino acid sequence as set forth in SEQ ID NO: 14, or an antigen-binding or an immunologically functional immunoglobulin fragment thereof, and the light chain comprises a light chain variable region comprising an amino acid sequence as set forth in SEQ ID NO: 16, or an antigen-binding or an immunologically functional immunoglobulin fragment thereof.

In certain aspects, the invention provides antibodies, which can specifically bind to and/or inhibit or modulate the biological activity of IFN-γ, comprising a heavy chain and a light chain, wherein the heavy chain comprises a heavy chain variable region, and wherein the heavy chain variable region comprises a sequence that has at least 80%, 85%, 90%, 91%, 92%, 93%, 94%, 95%, 96%, 97%, 98%, or about 99% identity to the amino acid sequence as set forth in SEQ ID NO: 14, and wherein the light chain comprises a light chain variable region, and wherein the light chain variable region comprises an amino acid sequence that has at least 80%, 85%, 90%, 91%, 92%, 93%, 94%, 95%, 96%, 97%, 98%, or about 99% identity to the amino acid sequence as set forth in SEQ ID NO: 16, wherein the antibody interacts with IFN-γ.

The invention also provides antibodies that can inhibit or modulate the biological activity of and/or bind specifically to IFN-γ, wherein the heavy chain comprises a heavy chain variable region comprising an amino acid sequence as set forth in SEQ ID NO: 14, or an antigen-binding or an immunologically functional immunoglobulin fragment thereof, and the light chain comprises a light chain variable region comprising an amino acid sequence as set forth in SEQ ID NO: 31, or an antigen-binding or an immunologically functional immunoglobulin fragment thereof.

In certain aspects, the invention provides antibodies, which can inhibit or modulate the biological activity of and/or specifically bind to IFN-γ, comprising a heavy chain and a light chain, wherein the heavy chain comprises a heavy chain variable region, and wherein the heavy chain variable region comprises a sequence that has at least 80%, 85%, 90%, 91%, 92%, 93%, 94%, 95%, 96%, 97%, 98%, or about 99% identity to the amino acid sequence as set forth in SEQ ID NO: 14, and wherein the light chain comprises a light chain variable region, and wherein the light chain variable region comprises an amino acid sequence that has at least 80%, 85%, 90%, 91%, 92%, 93%, 94%, 95%, 96%, 97%, 98%, or about 99% identity to the amino acid sequence as set forth in SEQ ID NO: 31, wherein the antibody interacts with IFN-γ.

The invention also provides antibodies that can inhibit or modulate the biological activity of and/or bind specifically to IFN-γ, wherein the heavy chain comprises an amino acid sequence as set forth in SEQ ID NO: 17 or an antigen-binding or an immunologically functional immunoglobulin fragment thereof, and the light chain comprises an amino acid sequence as set forth in SEQ ID NO: 18, or an antigen-binding or an immunologically functional immunoglobulin fragment thereof.

In certain aspects, the invention provides antibodies, which can inhibit or modulate the biological activity of and/or bind specifically to IFN-γ, comprising a heavy chain and a light chain, wherein the heavy chain comprises a heavy chain variable region, and wherein the heavy chain variable region comprises a sequence that has at least 80%, 85%, 90%, 91%, 92%, 93%, 94%, 95%, 96%, 97%, 98%, or about 99% identity to the amino acid sequence as set forth in SEQ ID NO: 17, and wherein the light chain comprises a light chain variable region, and wherein the light chain variable region comprises an amino acid sequence that has at least 80%, 85%, 90%, 91%, 92%, 93%, 94%, 95%, 96%, 97%, 98%, or about 99% identity to the amino acid sequence as set forth in SEQ ID NO: 18, wherein the antibody interacts with IFN-γ.

The invention further provides antibodies that can inhibit or modulate the biological activity of and/or bind specifically to IFN-γ, wherein the heavy chain comprises an amino acid sequence as set forth in SEQ ID NO: 19, or an antigen-binding or an immunologically functional immunoglobulin fragment thereof, and the light chain comprises an amino acid sequence as set forth in SEQ ID NO: 20, or an antigen-binding or an immunologically functional immunoglobulin fragment thereof.

In certain aspects, the invention provides antibodies, which can inhibit or modulate the biological activity of and/or bind specifically to IFN-γ, comprising a heavy chain and a light chain, wherein the heavy chain comprises a heavy chain variable region, and wherein the heavy chain variable region comprises a sequence that has at least 80%, 85%, 90%, 91%, 92%, 93%, 94%, 95%, 96%, 97%, 98%, or about 99% identity to the amino acid sequence as set forth in any of SEQ ID NO: 19, and wherein the light chain comprises a light chain variable region, and wherein the light chain variable region comprises an amino acid sequence that has at least 80%, 85%, 90%, 91%, 92%, 93%, 94%, 95%, 96%, 97%, 98%, or about 99% identity to the amino acid sequence as set forth in SEQ ID NO: 20, wherein the antibody interacts with IFN-γ.

The invention also provides antibodies that can inhibit or modulate the biological activity of and/or bind specifically to IFN-γ, wherein the heavy chain comprises an amino acid sequence as set forth in SEQ ID NO: 21, or an antigen-binding or an immunologically functional immunoglobulin fragment thereof, and the light chain comprises an amino acid sequence as set forth in SEQ ID NO: 22, or an antigen-binding or an immunologically functional immunoglobulin fragment thereof.

In certain aspects, the invention provides antibodies, which can inhibit or modulate the biological activity of and/or bind specifically to IFN-γ, comprising a heavy chain and a light chain, wherein the heavy chain comprises a heavy chain variable region, and wherein the heavy chain variable region comprises a sequence that has at least 80%, 85%, 90%, 91%, 92%, 93%, 94%, 95%, 96%, 97%, 98%, or about 99% identity to the amino acid sequence as set forth in any of SEQ ID NO: 21, and wherein the light chain comprises a light chain variable region, and wherein the light chain variable region comprises an amino acid sequence that has at least 80%, 85%, 90%, 91%, 92%, 93%, 94%, 95%, 96%, 97%, 98%, or about 99% identity to the amino acid sequence as set forth in SEQ ID NO: 22, wherein the antibody interacts with IFN-γ.

The invention also provides antibodies that can inhibit or modulate the biological activity of and/or bind specifically to IFN-γ, wherein the heavy chain comprises an amino acid sequence as set forth in SEQ ID NO: 32, or an antigen-binding or an immunologically functional immunoglobulin fragment thereof, and the light chain comprises an amino acid sequence as set forth in SEQ ID NO: 20, or an antigen-binding or an immunologically functional immunoglobulin fragment thereof.

In certain aspects, the invention provides antibodies, which can inhibit or modulate the biological activity of and/or bind specifically to IFN-γ, comprising a heavy chain and a light chain, wherein the heavy chain comprises a heavy chain variable region, and wherein the heavy chain variable region comprises a sequence that has at least 80%, 85%, 90%, 91%, 92%, 93%, 94%, 95%, 96%, 97%, 98%, or about 99% identity to the amino acid sequence as set forth in SEQ ID NO: 32, and wherein the light chain comprises a light chain variable region, and wherein the light chain variable region comprises an amino acid sequence that has at least 80%, 85%, 90%, 91%, 92%, 93%, 94%, 95%, 96%, 97%, 98%, or about 99% identity to the amino acid sequence as set forth in SEQ ID NO: 20, wherein the antibody interacts with IFN-γ.

The invention also provides antibodies that can inhibit or modulate the biological activity of and/or bind specifically to IFN-γ, wherein the heavy chain comprises an amino acid sequence as set forth in SEQ ID NO: 21, or an antigen-binding or an immunologically functional immunoglobulin fragment thereof, and the light chain comprises an amino acid sequence as set forth in SEQ ID NO: 33, or an antigen-binding or an immunologically functional immunoglobulin fragment thereof.

In certain aspects, the invention provides antibodies, which can inhibit or modulate the biological activity of and/or bind specifically to IFN-γ, comprising a heavy chain and a light chain, wherein the heavy chain comprises a heavy chain variable region, and wherein the heavy chain variable region comprises a sequence that has at least 80%, 85%, 90%, 91%, 92%, 93%, 94%, 95%, 96%, 97%, 98%, or about 99% identity to the amino acid sequence as set forth in SEQ ID NO: 21, and wherein the light chain comprises a light chain variable region, and wherein the light chain variable region comprises an amino acid sequence that has at least 80%, 85%, 90%, 91%, 92%, 93%, 94%, 95%, 96%, 97%, 98%, or about 99% identity to the amino acid sequence as set forth in SEQ ID NO: 33, wherein the antibody interacts with IFN-γ.

The invention also provides single chain antibodies, single chain Fv antibodies, F(ab) antibodies, F(ab)' antibodies and (Fab')₂ antibodies.

In particular aspects, the invention provides a light chain comprising an amino acid sequence as set forth in any of SEQ ID NO: 8, SEQ ID NO: 12, SEQ ID NO: 16, SEQ ID NO: 18, SEQ ID NO: 20, SEQ ID NO: 22, SEQ ID NO: 31, or SEQ ID NO: 33 or an antigen-binding or an immunologically functional immunoglobulin fragment thereof.

In addition, the invention provides a heavy chain comprising an amino acid sequence as set forth in any of SEQ ID NO: 6, SEQ ID NO: 10, SEQ ID NO: 14, SEQ ID NO: 17, SEQ ID NO: 19, SEQ ID NO: 21, SEQ ID NO: 30, or SEQ ID NO: 32, or an antigen-binding or an immunologically functional immunoglobulin fragment thereof.

The invention also relates to isolated human antibodies that specifically bind IFN-γ, wherein the antibody comprises: (a) human heavy chain framework regions, a human heavy chain CDR1 region, a human heavy chain CDR2 region, and a human heavy chain CDR3 region; and (b) human light chain framework regions, a human light chain CDR1 region, a human light chain CDR2 region, and a human light chain CDR3 region. In certain aspects, the human heavy chain CDR1 region can be the heavy chain CDR1 region of monoclonal antibodies (mAbs) 1119, 1118, 1118*, or 1121 as shown in FIG. 12 and SEQ ID NO:34 and the human light chain CDR1 region can be the light chain CDR1 region of mAbs 1119, 1118, 1121*, or 1121 as shown in FIG. 13 and SEQ ID NO:38, SEQ ID NO:39, or SEQ ID NO:40. In other aspects, the human heavy chain CDR2 region can be the heavy chain CDR2 region of mAbs 1119, 1118, 1118*, or 1121 as shown in FIG. 12 and SEQ ID NO:35 and the human light chain CDR2 region can be the light chain CDR2 region of mAbs 1119, 1118, 1121*, or 1121 as shown in FIG. 13 and SEQ ID NO:41 or SEQ ID NO:42. In still other aspects, the human heavy chain CDR3 region is the heavy chain CDR3 region of mAbs 1119, 1118, 1118*, or 1121 as shown in FIG. 12 and SEQ ID NO:36 or SEQ ID NO:37, and the human light chain CDR3 region is the light chain CDR3 region of mAbs 1119, 1118, 1121*, or 1121 as shown in FIG. 13 and SEQ ID NO:43 or SEQ ID NO:44.

In addition, the invention provides methods for treating a disease associated with increased production of or sensitivity to IFN-γ and/or a disease mediated by IFN-γ comprising the step of administering a pharmaceutically effective amount of one or a plurality of monoclonal antibodies of the invention or an antigen-binding or an immunologically functional immunoglobulin fragment thereof to an individual in need thereof.

The invention also provides methods for detecting the level of IFN-γ in a biological sample, comprising the step of contacting the sample with a monoclonal antibody of the invention or antigen-binding fragment thereof.

The invention also provides an isolated antibody that can bind specifically to and/or inhibit or modulate the biological activity of IFN-γ and comprises a heavy chain CDR3 having an amino acid sequence that is: (a) an amino acid sequence consisting of at least 7 of the amino acids of SEQ ID NO:36 in the same order and spacing as they occur in SEQ ID NO:36; or (b) an amino acid sequence comprising SEQ ID NO:37. The antibody can further comprise a light chain CDR3 having an amino acid sequence that is: (a) an amino acid sequence consisting at least 8 of the amino acids of SEQ ID NO:43 in the same order and spacing as they are in SEQ ID NO:43; or (b) an amino acid sequence consisting of at least 9 of the amino acids of SEQ ID NO:44 in the same order and spacing as they are in SEQ ID NO:44. The antibody can further comprise one or more CDR selected from the group consisting of: SEQ ID NO:34, SEQ ID NO:35, SEQ ID NO:38, SEQ ID NO:39, SEQ ID NO:40, SEQ ID NO:41, and SEQ ID NO:42. The heavy chain CDR3 may consist of at least the amino acids of SEQ ID NO:36 and the light chain CDR3 may consist of at least the amino acids of SEQ ID NO:43.

In addition, the invention provides isolated antibodies that can bind specifically to and/or inhibit or modulate the biological activity of IFN-γ comprising a light chain CDR3 having an amino acid sequence that is: (a) an amino acid sequence consisting of at least 8 of the amino acids of SEQ ID NO:43 in the same order and spacing as they occur in SEQ ID NO:43; or (b) an amino acid sequence consisting of at least 9 of the amino acids of SEQ ID NO:44 in the same order and spacing as they occur in SEQ ID NO:44. The antibody can further comprise a CDR having the amino acid sequence of SEQ ID NO:35, SEQ ID NO:38, SEQ ID NO:39, SEQ ID NO:40, SEQ ID NO:41, or SEQ ID NO:42.

An isolated antibody of the invention, which can specifically bind to and/or inhibit or modulate the biological activity of IFN-γ, can comprise six CDRs having at least the amino acid sequences of: (a) SEQ ID NO:34; (b) SEQ ID NO:35; (c) SEQ ID NO:36 or SEQ ID NO:37; (d) SEQ ID NO:38, SEQ ID NO:39, or SEQ ID NO:40; (e) SEQ ID NO:41 or SEQ ID NO:42; and (f) SEQ ID NO:43 or SEQ ID NO:44.

Isolated antibodies of the invention, which can specifically bind to and/or inhibit or modulate the biological activity of IFN-γ, can comprise an amino acid sequence at least 80%, 85%, 90%, 91%, 92%, 93%, 94%, 95%, 96%, 97%, 98%, or about 99% identical to SEQ ID NO:6, SEQ ID NO:10, SEQ ID NO:14, or SEQ ID NO:30, wherein the alignment between the amino acid sequence and SEQ ID NO:6, SEQ ID NO:10, SEQ ID NO:14, or SEQ ID NO:30 spans at least 50 amino acids, and/or an amino acid sequence at least 80%, 85%, 90%, 91%, 92%, 93%, 94%, 95%, 96%, 97%, 98%, or about 99% identical to SEQ ID NO:8, SEQ ID NO:12, SEQ ID NO:16, or SEQ ID NO:31, wherein the alignment between the amino acid sequence and SEQ ID NO:8, SEQ ID NO:12, SEQ ID NO:16, or SEQ ID NO:31 spans at least 50 amino acids.

In another aspect, antibodies of the invention, which can specifically bind to and/or inhibit or modulate the biological activity of IFN-γ, can comprise an amino acid sequence at least 80%, 85%, 90%, 91%, 92%, 93%, 94%, 95%, 96%, 97%, 98%, or about 99% identical to SEQ ID NO:17, SEQ ID NO:19, SEQ ID NO:21, or SEQ ID NO:32, wherein the alignment between the amino acid sequence and SEQ ID NO:17, SEQ ID NO:19, SEQ ID NO:21, or SEQ ID NO:32 spans at least 50 amino acids, and/or an amino acid sequence at least 80%, 85%, 90%, 91%, 92%, 93%, 94%, 95%, 96%, 97%, 98%, or about 99% identical to SEQ ID NO:18, SEQ ID NO:20, SEQ ID NO:22, or SEQ ID NO:33, wherein the alignment between the amino acid sequence and SEQ ID NO:18, SEQ ID NO:20, SEQ ID NO:22, or SEQ ID NO:33 spans at least 50 amino acids. One amino acid sequence within these antibodies can comprise at least 5 of the amino acids in SEQ ID NO:36 or SEQ ID NO:37, in the same order and spacing as they occur in SEQ ID NO:36 or SEQ ID NO:37, and/or one amino acid sequence within these antibodies can comprise at least 6 of the amino acids in SEQ ID NO:43 or SEQ ID NO:44 in the same order and spacing as they occur in SEQ ID NO:43 or SEQ ID NO:44.

In one aspect, the invention provides an antibody, which can be an isolated fully human antibody, wherein the antibody can inhibit or modulate the biological activity of human IFN-γ. In another aspect, an antibody of the invention, which can be an isolated fully human antibody, cannot inhibit or modulate the biological activity of cynomolgus monkey and murine IFN-γ. In yet another aspect, a fully human antibody of the invention can inhibit or modulate the biological activity of human and chimpanzee IFN-γ, but cannot inhibit or modulate the biological activity of cynomolgus monkey and/or murine IFN-γ. In still another aspect, substitution of residue 19 of human IFN-γ with aspartic acid and/or residue 20 with proline prevents or antagonizes the inhibition of the biological activity of human IFN-γ by the antibody. Further, the antibody can inhibit the biological activity of a mutated version of cynolmolgus monkey IFN-γ substituted at residues 19, 20, and 65 with histidine, serine, and serine, respectively.

In yet further aspects, isolated antibodies of the invention, which can bind specifically to and/or inhibit or modulate the biological activity of IFN-γ, can comprise an amino acid sequence at least 80%, 85%, 90%, 91%, 92%, 93%, 94%, 95%, 96%, 97%, 98%, or about 99% identical to SEQ ID NO:17, SEQ ID NO:19, SEQ ID NO:21, or SEQ ID NO:32, wherein the alignment between the amino acid sequence and SEQ ID NO:17, SEQ ID NO:19, SEQ ID NO:21, or SEQ ID NO:32 spans at least 50 amino acids, and/or can comprise an amino acid sequence at least 80%, 85%, 90%, 91%, 92%, 93%, 94%, 95%, 96%, 97%, 98%, or about 99% identical to SEQ ID NO:18, SEQ ID NO:20, SEQ ID NO:22, or SEQ ID NO:33, wherein the alignment between the amino acid sequence and SEQ ID NO:18, SEQ ID NO:20, SEQ ID NO:22, or SEQ ID NO:33 spans at least 50 amino acids.

In a further embodiment, the invention encompasses an isolated antibody that can bind specifically to IFN-γ comprising (a) an amino acid sequence comprising SEQ ID NO:6, SEQ ID NO:10, SEQ ID NO:14, or SEQ ID NO:30, or a fragment of one of these sequences and (b) an amino acid sequence comprising SEQ ID NO:8, SEQ ID NO:12, SEQ ID NO:16, or SEQ ID NO:31, or a fragment of one of these sequences. The antibody may comprise a heavy chain and a light chain. The antibody may comprise (a) SEQ ID NO:6, SEQ ID NO:10, SEQ ID NO:14, or SEQ ID NO:30 and (b) SEQ ID NO:8, SEQ ID NO:12, SEQ ID NO:16, or SEQ ID NO:31.

Further, any of the antibodies of the invention can be humanized antibodies or fully human antibodies.

The invention also provides polynucleotides, including isolated polynucleotides, that encode any of the antibodies of the invention or portions thereof as described herein, including CDR regions, heavy chain variable regions, light chain variable regions, single chain antibodies, single chain Fv antibodies, F(ab) antibodies, F(ab)' antibodies and $(Fab')_2$ antibodies. The invention further provides vectors comprising such polynucleotides and host cells, optionally mammalian host cells, containing such polynucleotides and/or vectors. Antibodies of the invention can be produced by culturing such host cells.

Specific preferred embodiments of the invention will become evident from the following more detailed description of certain preferred embodiments and the claims.

BRIEF DESCRIPTION OF THE DRAWINGS

FIGS. 1A-1B depict a nucleotide sequence of a portion of a cDNA (FIG. 1A; SEQ ID NO:1) encoding an amino acid sequence (FIG. 1B; SEQ ID NO:2) of a heavy chain constant region of the 1118, 1118*, 1119, 1121, and 1121* anti-IFN-γ antibodies.

FIGS. 2A-2B depict the nucleotide sequence of a portion of a cDNA (FIG. 2A; SEQ ID NO:3) encoding an amino acid sequence (FIG. 2B; SEQ ID NO:4) of a light chain constant region of the 1118, 1118*, 1119, 1121, and 1121* anti-IFN-γ antibodies.

FIGS. 3A-3B depict the nucleotide sequence of a portion of a cDNA (FIG. 3A; SEQ ID NO:5) encoding an amino acid sequence (FIG. 3B; SEQ ID NO:6) of the heavy chain variable region of the 1119 anti-IFN-γ antibody.

FIGS. 4A-4B depict the nucleotide sequence of a portion of a cDNA (FIG. 4A; SEQ ID NO:7) encoding an amino acid sequence (FIG. 4B; SEQ ID NO: 8) of the light chain variable region of the 1119 anti-IFN-γ antibody.

FIG. 5A-5B depict the nucleotide sequence of a portion of a cDNA (FIG. 5A; SEQ ID NO: 9) encoding the amino acid sequence (FIG. 5B; SEQ ID NO:10) of the heavy chain variable region of the 1118 anti-IFN-γ antibody. FIG. 5C depicts the amino acid sequence of the heavy chain variable region (SEQ ID NO:30) of the 1118* anti-IFN-γ antibody. FIG. 5D depicts the nucleotide sequence of the heavy chain variable region (SEQ ID NO:56) of the 1118* anti-IFN-γ antibody.

FIGS. 6A-6B depict the nucleotide sequence of a portion of a cDNA (FIG. 6A; SEQ ID NO:11) encoding the amino acid sequence (FIG. 6B; SEQ ID NO:12) of the light chain variable region of the 1118 or 1118* anti-IFN-γ antibody.

FIGS. 7A-7B depict the nucleotide sequence of a portion of a cDNA (FIG. 7A; SEQ ID NO:13) encoding the amino acid sequence (FIG. 7B; SEQ ID NO:14) of the heavy chain variable region of the 1121 or 1121* anti-IFN-γ antibody.

FIG. 8A-B depict the nucleotide sequence of a portion of a cDNA (FIG. 8A; SEQ ID NO:15) encoding the amino acid sequence (FIG. 8B; SEQ ID NO:16) of the light chain variable region of the 1121 anti-IFN-γ antibody. FIG. 8C depicts the amino acid sequence (SEQ ID NO:31) of the light chain variable region of the 1121* anti-IFN-γ antibody. FIG. 8D depicts the nucleotide sequence (SEQ ID NO:57) of the light chain variable region of the 1121* anti-IFN-γ antibody.

FIG. 9 contains a graph showing neutralization or inhibition of the biological activity of IFN-γ in the A549 bioassay with the 1119, 1118, and 1121 monoclonal antibodies.

FIG. 10 contains a graph showing neutralization or inhibition of the biological activity of IFN-γ in the THP-1/HLA DR bioassay by the 1119, 1118, and 1121 monoclonal antibodies.

FIG. 11 contains a graph showing neutralization or inhibition of the biological activity of IFN-γ in a whole blood bioassay (two donors) by the 1119 monoclonal antibody.

FIG. 12 shows an alignment of an amino terminal portion (including the variable region) of the heavy chains of the anti-IFN-γ monoclonal antibodies designated 1118, 1118*, 1121, and 1119. The sequences include the signal sequence encoded on the cDNAs isolated in Example 3. The signal sequence extends from position 1 through 19. CDRs are underlined. As depicted in the Figure, CDR1 spans from amino acid 50-54, CDR2 spans from 69-85, and CDR3 spans from 118-125. The numbering system of Kabat et al. (1991, Sequences of Proteins of Immunological Interest, Public Health Service N.I.H., Bethesda, Md.) starts at the first amino acid of the mature antibody and excludes the signal sequence. Thus, position 20 in this Figure would correspond to position 1 of Kabat et al. (supra).

FIG. 13 shows an alignment of an amino terminal portion (including the variable region) of the light chains of the anti-IFN-γ monoclonal antibodies designated 1118, 1121, 1121*, and 1119. The sequences include the signal sequence encoded on the cDNAs isolated in Example 3. The signal sequence extends from position 1 through 20. CDRs are underlined. As depicted in the Figure, CDR1 spans from amino acid 44-55, CDR2 spans from 71-77, and CDR3 spans from 110-118. Since the numbering system of Kabat et al. (supra) excludes the signal sequence, position 21 in this Figure corresponds to position 1 of Kabat et al.

DETAILED DESCRIPTION OF THE INVENTION

Figure 9:
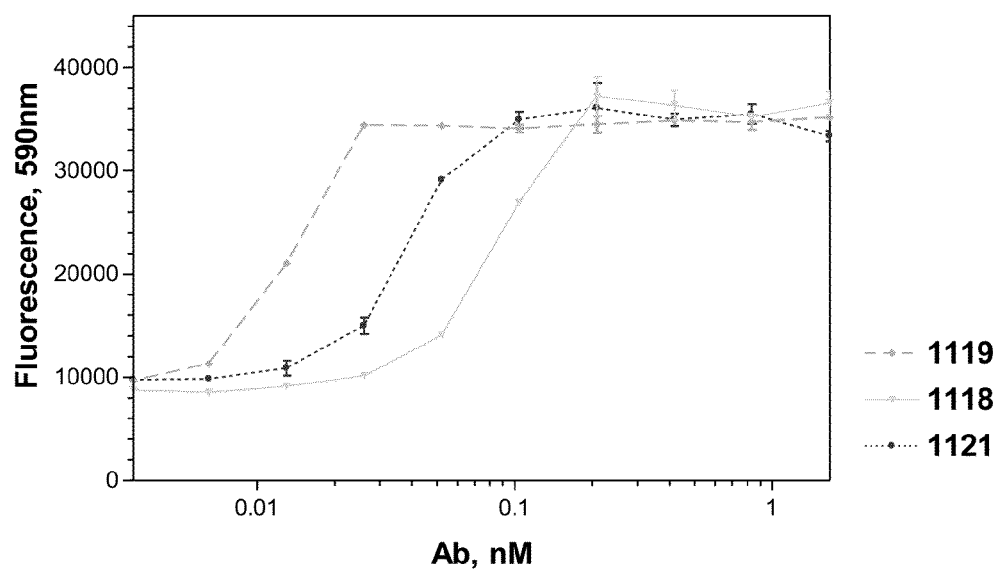

The section headings used herein are for organizational purposes only and are not to be construed as limiting the subject matter described. All references cited in this application are expressly incorporated by reference herein for any purpose.

DEFINITIONS

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., 2001, MOLECULAR CLONING: A LABORATORY MANUAL, 3d ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

As utilized in accordance with the present disclosure, the following terms, unless otherwise indicated, shall be understood to have the following meanings.

The term "isolated polynucleotide" as used herein shall mean a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of synthetic origin, or any combination thereof. Preferably, the isolated protein is substantially free from proteins or polypeptides or other contaminants that are found in its natural environment that would interfere with its use (therapeutic, diagnostic, prophylactic, research or otherwise).

The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass anti-IFN-γ antibodies, or sequences that have deletions from, additions to, and/or substitutions of one or more amino acid of an anti-IFN-γ antibody. Thus, a "polypeptide" or a "protein" can comprising one (termed "a monomer") or a plurality (termed "a multimer") of amino acid chains.

The term "polypeptide fragment" refers to a polypeptide, which can be monomeric or multimeric, that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 5, 6, 8, 10, 14, 20, 50, 70, 100, 110, 150, 200, 250, 300, 350, 400, or 450 amino acids long. Particularly useful polypeptide fragments include functional domains, including binding domains. In the case of an anti-IFN-γ antibody, useful fragments include, but are not limited to: a CDR region, especially a CDR3 region of the heavy or light chain; a variable domain of a heavy or light chain; a portion of an antibody chain or just its variable region including two CDRs; and the like.

The term "immunologically functional immunoglobulin fragment" as used herein refers to a polypeptide fragment that contains at least the CDRs of the immunoglobulin heavy and light chains. An immunologically functional immunoglobulin fragment of the invention is capable of binding to an antigen. In preferred embodiments, the antigen is a ligand that specifically binds to a receptor. In these embodiments, binding of an immunologically functional immunoglobulin fragment of the invention prevents or inhibits binding of the ligand to its receptor, interrupting the biological response resulting from ligand binding to the receptor. Preferably, an immunologically functional immunoglobulin fragment of the invention binds specifically to IFN-γ. Most preferably, the fragment binds specifically to and/or inhibits or modulates the biological activity of human IFN-γ.

The term "naturally-occurring" as used herein and applied to an object refers to the fact that the object can be found in nature. For example, a polypeptide or polynucleotide sequence that is present in an organism (including viruses) that can be isolated from a source in nature and that has not been intentionally modified by man is naturally-occurring.

The term "operably linked" means that the components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as referred to herein means single-stranded or double-stranded nucleic acid polymers of at least 10 bases in length. In certain embodiments, the nucleotides comprising the polynucleotide can be ribonucleotides or deoxyribonucleotides or a modified form of either type of nucleotide. Said modifications include base modifications such as bromuridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "oligonucleotide" referred to herein includes naturally occurring, and modified nucleotides linked together by naturally occurring, and/or non-naturally occurring oligonucleotide linkages. Oligonucleotides are a polynucleotide subset comprising members that are generally single-stranded and have a length of 200 bases or fewer. In certain embodiments, oligonucleotides are 10 to 60 bases in length. In certain embodiments, oligonucleotides are 12, 13, 14, 15, 16, 17, 18, 19, or 20 to 40 bases in length. Oligonucleotides may be single stranded or double stranded, e.g. for use in the construction of a gene mutant. Oligonucleotides of the invention may be sense or antisense oligonucleotides with reference to a protein-coding sequence.

Unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, *Nucl. Acids Res.*, 14:9081; Stec et al., 1984, *J. Am. Chem. Soc.*, 106:6077; Stein et al., 1988, *Nucl. Acids Res.*, 16:3209; Zon et al., 1991, *Anti-Cancer Drug Design*, 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990, *Chemical Reviews,* 90:543, the disclosures of which are hereby incorporated by reference for any purpose. An oligonucleotide can include a detectable label to enable detection of the oligonucleotide or hybridization thereof.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control expression of inserted heterologous nucleic acid sequences. Expression includes, but is not limited to, processes such as transcription, translation, and RNA splicing, if introns are present.

The term "host cell" is used to refer to a cell into which has been introduced, or is capable of being introduced with a nucleic acid sequence and further expresses or is capable of expressing a selected gene of interest. The term includes the progeny of the parent cell, whether or not the progeny is identical in morphology or in genetic make-up to the original parent, so long as the selected gene is present.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., 2001, MOLECULAR CLONING, A LABORATORY MANUAL, Cold Spring Harbor Laboratories; Davis et al., 1986, BASIC METHODS IN MOLECULAR BIOLOGY, Elsevier; and Chu et al., 1981, *Gene* 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl, or sulfonyl, and, in certain embodiments, may have specific three-dimensional structural characteristics, and/or specific charge characteristics. In certain embodiments, an antibody is said to specifically bind an antigen when it preferentially recognizes its target antigen in a complex mixture of proteins and/or macromolecules. An antibody is said to specifically bind an antigen when the equilibrium dissociation constant is $\leq 10^{-7}$ or $10^{-8}$ M. In some embodiments, the equilibrium dissociation constant may be $\leq 10^{-9}$ M or $\leq 10^{-10}$ M.

As used herein, when a first sequence consists of, for example, 10 amino acids of the sequence RASQSVSSSY (SEQ ID NO: 56), another sequence has 7 amino acids in the "same order and spacing" as they occur in the first sequence if 7 amino acids are identical to those in the sequence and occur in the same relative positions as they occur in the sequence. For example, a sequence RAAAAVSSSY (SEQ ID NO: 57) has 7 amino acids in the same order and spacing as they occur in RASQSVSSSY (SEQ ID NO: 56). In contrast, this is not true for a sequence RASSVSSSY (SEQ ID NO: 58), since it contains an internal deletion relative to RASQSVSSSY (SEQ ID NO: 56), with 3 and 6 amino acids on either side of the deletion. Therefore, it has at most 6 amino acids in the same order and spacing as the first sequence. The shortest possible sequence that could have 7 amino acids in the same order and spacing as in RASQSVSSSY (SEQ ID NO: 56) would be 7 amino acids long, for example SQSVSSS (SEQ ID NO: 59).

The term "identity," as known in the art, refers to a relationship between the sequences of two or more polypeptide molecules or two or more nucleic acid molecules, as determined by comparing the sequences thereof. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is used in the art with regard to a related concept, but in contrast to "identity," "similarity" refers to a measure of relatedness, which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

Identity and similarity of related nucleic acids and polypeptides can be readily calculated by known methods. Such methods include, but are not limited to, those described in COMPUTATIONAL MOLECULAR BIOLOGY, (Lesk, A. M., ed.), 1988, Oxford University Press, New York; BIOCOMPUTING: INFORMATICS AND GENOME PROJECTS, (Smith, D. W., ed.), 1993, Academic Press, New York; COMPUTER ANALYSIS OF SEQUENCE DATA, Part 1, (Griffin, A. M., and Griffin, H. G., eds.), 1994, Humana Press, New Jersey; von Heinje, G., SEQUENCE ANALYSIS IN MOLECULAR BIOLOGY, 1987, Academic Press; SEQUENCE ANALYSIS PRIMER, (Gribskov, M. and Devereux, J., eds.), 1991, M. Stockton Press, New York; Carillo et al., 1988, SIAM J. *Applied Math.*, 48:1073; and Durbin et al., 1998, BIOLOGICAL SEQUENCE ANALYSIS, Cambridge University Press.

Preferred methods to determine identity are designed to give the largest match between the sequences tested. Methods to determine identity are described in publicly available computer programs. Preferred computer program methods to determine identity between two sequences include, but are not limited to, the GCG program package, including GAP (Devereux et al., 1984, *Nucl. Acid. Res.*, 12:387; Genetics Computer Group, University of Wisconsin, Madison, Wis.), BLASTP, BLASTN, and FASTA (Altschul et al., 1990, *J. Mol. Biol.*, 215:403-410). The BLASTX program is publicly available from the National Center for Biotechnology Information (NCBI) and other sources (BLAST Manual, Altschul et al. NCB/NLM/NIH Bethesda, Md. 20894; Altschul et al., 1990, supra). The well-known Smith Waterman algorithm may also be used to determine identity.

Certain alignment schemes for aligning two amino acid or polynucleotide sequences may result in matching of only a short region of the two sequences, and this small aligned region may have very high sequence identity even though there is no significant relationship between the two full-length sequences. Accordingly, in certain embodiments, the selected alignment method (GAP program) will result in an alignment that spans at least 50 contiguous amino acids of the target polypeptide. In some embodiments, the alignment can comprise at least 60, 70, 80, 90, 100, 110, or 120 amino acids of the target polypeptide. If polynucleotides are aligned using GAP, the alignment can span at least about 100, 150, or 200 nucleotides, which can be contiguous.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is calculated as three-times the average diagonal; where the "average diagonal" is the average of the diagonal of the comparison matrix being used; the "diagonal" is the score or number assigned to each perfect amino acid match by the particular comparison matrix) and a gap extension penalty (which is usually one-tenth of the gap opening penalty), as well as a comparison matrix such as PAM250 or BLOSUM 62 are used in conjunction with the algorithm. In certain embodiments, a standard comparison matrix (see Dayhoff et al., 1978, *Atlas of Protein Sequence and Structure*, 5:345-352 for the PAM 250 comparison matrix; Henikoff et al., 1992, *Proc. Natl. Acad. Sci. USA*, 89:10915-10919 for the BLOSUM 62 comparison matrix) is also used by the algorithm.

In certain embodiments, the parameters for a polypeptide sequence comparison include the following:

Algorithm: Needleman et al., 1970, *J. Mol. Biol*, 48:443-453;

Comparison matrix: BLOSUM 62 from Henikoff et al., 1992, supra;

Gap Penalty: 12
Gap Length Penalty: 4
Threshold of Similarity: 0

The GAP program may be useful with the above parameters. For nucleotide sequences, parameters can include a gap penalty of 50 and a gap length penalty of 3, that is a penalty of 3 for each symbol in each gap. In certain embodiments, the aforementioned parameters are the default parameters for polypeptide comparisons (along with no penalty for end gaps) using the GAP algorithm.

As used herein, the twenty conventional amino acids and their abbreviations follow conventional usage. See IMMUNOLOGY—A SYNTHESIS, 2nd Edition, (E. S. Golub and D. R. Gren, Eds.), Sinauer Associates: Sunderland, Mass., 1991, incorporated herein by reference for any purpose. Stereoisomers (e.g., D-amino acids) of the twenty conventional amino acids; unnatural amino acids such as α-, α-disubstituted amino acids, N-alkyl amino acids, lactic acid, and other unconventional amino acids may also be suitable components for polypeptides of the invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

Naturally occurring residues may be divided into classes based on common side chain properties:

1) hydrophobic: norleucine (Nor), Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of these classes for a member from another class. Such substituted residues may be introduced into regions of the human antibody that are homologous with non-human antibodies, or into the non-homologous regions of the molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ille |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Scr | Scr |
| Trp | Tyr, Phe | Tyr |
| Tyr | Trp, Phe, Thr, Set | Phe |
| Val | Ile, Met, Leu, Phe, Ala, Norleucine | Leu |

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose to not make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See, for example, Moult, 1996, Curr. Op. in Biotech. 7:422-427; Chou et al., 1974, Biochemistry 13:222-245; Chou et al., 1974, Biochemistry 113:211-222; Chou et al., 1978, Adv. Enzymol. Relat. Areas Mol. Biol. 47:45-148; Chou et al., 1979, Ann. Rev. Biochem. 47:251-276; and Chou et al., 1979, Biophys. J. 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., 1999, Nucl. Acid. Res. 27:244-247. It has been suggested (Brenner et al., 1997, Curr. Op. Struct. Biol. 7:369-376) that there are a limited number of folds in a given polypeptide or protein and that once a critical number of structures have been resolved, structural prediction will become dramatically more accurate.

Additional methods of predicting secondary structure include "threading" (Jones, 1997, Curr. Opin. Struct. Biol. 7:377-87; Sippl et al., 1996, Structure 4:15-19), "profile analysis" (Bowie et al., 1991, Science 253:164-170; Gribskov et al., 1990, Meth. Enzym. 183:146-159; Gribskov et al., 1987, Proc. Nat. Acad. Sci. 84:4355-4358), and "evolutionary linkage" (See Holm, 1999, supra; and Brenner, 1997, supra).

According to certain embodiments, amino acid substitutions are those that: (1) reduce susceptibility to proteolysis, (2) reduce susceptibility to oxidation, (3) alter binding affinity for forming protein complexes, (4) alter binding affinities, and/or (5) confer or modify other physicochemical or functional properties on such polypeptides. According to certain embodiments, single or multiple amino acid substitutions (in certain embodiments, conservative amino acid substitutions) may be made in the naturally occurring sequence (in certain embodiments, in the portion of the polypeptide outside the domain(s) forming intermolecular contacts). In preferred embodiments, a conservative amino acid substitution typically does not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in PROTEINS, STRUCTURES AND MOLECULAR PRINCIPLES, (Creighton, Ed.), 1984, W. H. Freeman and Company, New York; INTRODUCTION TO PROTEIN STRUCTURE (C. Branden and J. Tooze, eds.), 1991, Garland Publishing, New York, N.Y.; and Thornton et al., 1991, *Nature* 354:105, each of which are incorporated herein by reference.

Peptide analogs are commonly used in the pharmaceutical industry as non-peptide drugs with properties analogous to those of the template peptide. These types of non-peptide compound are termed "peptide mimetics" or "peptidomimetics". See Fauchere, 1986, *Adv. Drug Res.* 15:29; Veber & Freidinger, 1985, TINS p. 392; and Evans et al., 1987, *J. Med. Chem.* 30:1229, which are incorporated herein by reference for any purpose. Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: $—CH_2—NH—$, $CH_2—S—$, $CH_2—CH_2—$, $CH=CH—$ (cis and trans), $—COCH_2—$, $CH(OH)CH_2—$, and $—CH_2SO—$, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo & Gierasch, 1992, *Ann. Rev. Biochem.* 61:387, incorporated herein by reference for any purpose); for example, by adding internal cysteine residues capable of forming intramolecular disulfide bridges which cyclize the peptide.

As used herein, the terms "antibody" or "antibody peptide(s)" refer to a monomeric or multimeric protein comprising one or more polypeptide chains. An antibody can bind specifically to an antigen and may be able to inhibit or modulate the biological activity of the antigen. "Antibodies" include naturally occurring antibodies, which are described below. In certain embodiments, antibodies are produced by recombinant DNA techniques. In additional embodiments, antibodies are produced by enzymatic or chemical cleavage of naturally occurring antibodies. Antibodies include, but are not limited to, F(ab), F(ab'), F(ab')$_2$, Fv, and single chain Fv fragments, as well as single-chain, chimeric, humanized, fully human, polyclonal, and monoclonal antibodies. At a minimum, an antibody, as meant herein, comprises a polypeptide that can bind specifically to an antigen comprising all or part of a light or heavy chain variable region.

A variable region comprises at least three heavy or light chain complementarity determining regions (CDRs, also known as hypervariable regions, designated CDR1, CDR2, and CDR3 by Kabat et al., 1991, Sequences of Proteins of Immunological Interest, Public Health Service N.I.H., Bethesda, Md.; see also Chothia and Lesk, 1987, J. Mol. Biol. 196: 901-17; Chothia et al., 1989, Nature 342: 877-83) embedded within a framework region (designated framework regions 1-4, FR1, FR2, FR3, and FR4, by Kabat et al., supra; see also Chothia and Lesk, supra). The CDRs and the framework segments are interspersed as follow, starting at the amino terminus of the variable region: FR1-CDR1-FR2-CDR2-FR3-CDR3-FR4.

The primary sequences of the framework regions of antibody variable regions have a handful of residues that are universally conserved across phyla. However, many residues are highly conserved across phyla and/or within species and/or phyla, and many positions within antibodies are usually occupied by one of a known group of amino acids. See Kabat et al., supra. Alternatively a sequence can be recognized as an antibody by its predicted tertiary structure. The tertiary structure of the variable regions, which comprises 9 β strands forming a structure known as a Greek key β barrel, is extremely well conserved, and the positions of the CDRs within this structure are also highly conserved. See e.g., Bork et al., 1994, J. Mol. Biol. 242: 309-20; Hunkapiller and Hood, 1989, Adv. Immunol. 44: 1-63; Williams and Barclay, 1988, Ann. Rev. Immunol. 6: 381-405; Chothia and Lesk, supra; Kabat et al., supra.

Tertiary structure can be predicted by various computer programs, such as, for example, GENEFOLD® (Tripos, Inc., St. Louis, Mo.; Godzik and Skolnik, 1992, Proc. Natl. Acad. Sci. USA 89: 12098-12102; Godzik et al., 1992, J. Mol. Biol. 227: 227-38; Godzik et al., 1993, Protein Engng. 6: 801-10), a protein threading program that overlays a query protein sequence onto structural representatives of the Protein Data Bank (PDB) (Berman et al., 2000, *Nucleic Acids Res* 28: 235-242; Jaroszewski et al., 1998, *Prot Sci* 7: 1431-1440). To use GENEFOLD® to classify a new amino acid sequence, the sequence is entered into the program, which assigns a probability score that reflects how well it folds onto previously known protein structures ("template" structures) that are present in the GENEFOLD® database. For scoring, GENEFOLD® relies on primary amino acid sequence similarity, burial patterns of residues, local interactions and secondary structure comparisons. The GENEFOLD® program folds (or threads) the amino acid sequence onto all of the template structures in a preexisting database of protein folds, which includes the solved structures for a number of antibodies. The output of GENEFOLD® is three lists of proteins from within the database, the tertiary structures of which are the most likely to be assumed by the input amino acid sequence. The three lists contain three different scores calculated based on (i) sequence only, (ii) sequence plus local conformation preferences plus burial terms, and (iii) sequence plus local conformation preferences plus burial terms plus secondary structure. In each instance, the program determines the optimal alignment, calculates the probability (P-value) that this degree of alignment occurred by chance, and reports the inverse of the P-value as the score with 999.9 ($9.999 \times 10^2$) being the highest possible score. Thus, the highest score indicates the lowest probability that the alignment occurred by chance. These scores therefore reflect the degree to which the new protein matches the various reference structures and are useful for assigning a new protein to membership in a known family of proteins. For example, a sequence having the structure of an antibody variable region would be expected to be aligned with at least one known antibody variable region with a reasonably high P-value, such as at least about 200, 300, 400, 500, 600, 700, 800, or higher.

The term "heavy chain" includes any immunoglobulin polypeptide having sufficient variable region sequence to confer binding specificity for IFN-γ. The term "light chain" includes any immunoglobulin polypeptide having sufficient variable region sequence to confer binding specificity for IFN-γ. Such a heavy or light chain may, but need not, bind to IFN-γ in the absence of a light chain, if it is a heavy chain, or a heavy chain, if it is a light chain. A full-length heavy chain includes a variable region domain, $V_H$, and three constant region domains, $C_{H1}$, $C_{H2}$, and $C_{H3}$. The $V_H$ domain is at the amino-terminus of the polypeptide, and the $C_{H3}$ domain is at the carboxyl-terminus. The term "heavy chain", as used herein, encompasses a full-length heavy chain and fragments thereof. A full-length light chain includes a variable region domain, $V_L$, and a constant region domain, $C_L$. Like the heavy chain, the variable region domain of the light chain is at the amino-terminus of the polypeptide. The term "light chain", as used herein, encompasses a full-length light chain and fragments thereof. An F(ab) fragment is comprised of one light chain and the $C_{H1}$ and variable regions of one heavy chain. The heavy chain of an F(ab) molecule cannot form a disulfide bond with another heavy chain molecule. An F(ab') fragment contains one light chain and one heavy chain that contains more of the constant region, between the $C_{H1}$ and $C_{H2}$ domains, such that an interchain disulfide bond can be formed between two heavy chains to form an F(ab')$_2$ molecule. The Fv region comprises the variable regions from both the heavy and light chains, but lacks the constant regions. Single-chain antibodies are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203.

The invention also encompasses fully human, humanized, and chimeric antibodies. As meant herein, fully human antibodies comprise amino acid sequences encoded only by polynucleotides that are ultimately of human origin or amino acid sequences that are identical to such sequences. As meant herein, antibodies encoded by human immunoglobulin-encoding DNA inserted into a mouse genome produced in a transgenic mouse are fully human antibodies since they are encoded by DNA that is ultimately of human origin. In this situation, human immunoglobulin-encoding DNA can be rearranged (to encode an antibody) within the mouse, and somatic mutations may also occur. Antibodies encoded by originally human DNA that has undergone such changes in a mouse are fully human antibodies as meant herein. The use of such transgenic mice makes it possible to select fully human antibodies against a human antigen. In nature, this is not possible in most instances since a human immune response against a self antigen does not normally occur. One of skill in the art will appreciate that fully human antibodies are advantageous for use as therapeutics, particularly to treat chronic diseases, since they are unlikely to precipitate an immune response against themselves. In contrast, many non-human antibodies are known to precipitate an immune response against themselves when used in humans, a situation that makes chronic use of such antibodies in humans inadvisable. Fully human antibodies thus solve a long-standing problem faced in using antibodies to treat chronic conditions, including human diseases. See e.g. Billiau, 1988, *Immunol. Today* 9:37-40; Horneff et al., 1991, *Clin. Immunol. & Immunopathol.* 59:89-103; Tjandra et al., 1990, *Immunol & Cell Biol.* 68:367-76. Therefore, fully human anti-IFN-γ antibodies are particularly well suited for the treatment of chronic human IFN-γ mediated diseases, such as autoimmune diseases.

In a humanized antibody, the entire antibody, except the CDRs, is encoded by a polynucleotide of human origin or is identical to such an antibody except within its CDRs. The CDRs, which are encoded by nucleic acids originating in a non-human organism, are grafted into the β-sheet framework of a human antibody variable region to create an antibody, the specificity of which is determined by the engrafted CDRs. The creation of such antibodies is described in, e.g., WO 92/11018, Jones et al., 1986, *Nature* 321:522-25, Verhoeyen et al., 1988, *Science* 239:1534-36. This work underlines the pivotal importance of the CDRs in forming an antigen binding site. A chimeric antibody comprises a human constant region (which is encoded by a polynucleotide of human origin or is identical to such an human constant region) and a non-human variable region. The creation of such antibodies is described in, e.g., U.S. Pat. No. 5,681,722.

A bivalent antibody other than a "multispecific" or "multifunctional" antibody, in certain embodiments, is understood to comprise binding sites having identical antigenic specificity.

In assessing antibody binding and specificity according to the invention, an antibody binds specifically and/or substantially inhibits adhesion of a IFN-γ to its receptor when an excess of antibody reduces the quantity of receptor bound to IFN-γ, or vice versa, by at least about 20%, 40%, 60%, 80%, 85%, or more (as measured in an in vitro competitive binding assay). A specifically-binding antibody can be expected to have an equilibrium dissociation constant for binding to IFN-γ of less than or equal to than $10^{-8}$ molar, optionally less than or equal to $10^{-9}$ or $10^{-10}$ molar.

For therapeutic use, an important characteristic of an anti-IFN-γ antibody is whether it can inhibit or modulate the biological activity of IFN-γ. IFN-γ has many distinct biological effects, which can be measured in many different assays in different cell types. The ability of an anti-IFN-γ antibody to inhibit or modulate the biological activity of IFN-γ can be measured using the A549 assay described in Example 6 below or using a similar assay in which the ability of an antibody to reverse the inhibition of cell proliferation observed in the presence of IFN-γ is measured. For the assay to produce meaningful results, the proliferation of the cells used in the assay must be inhibited by the IFN-γ used in the assay. Human IFN-γ can inhibit proliferation of some cell types, including A549 cells (Examples 6 and 7). Murine IFN-γ can inhibit the proliferation of RAW 264.7 cells (Example 7), but not A549 cells. Especially when testing the ability of an antibody to inhibit or modulate the biological activity of a non-human IFN-γ cell types other than A549 cells can be used since non-human IFN-γ may or may not be able to inhibit proliferation of A549 cells. Not every antibody that specifically binds to an antigen can block antigen binding to its normal receptor and thus inhibit or modulate the biological effects of the antigen upon binding to its receptor. As is known in the art, such an effect can depend on what portion of the antigen the antibody binds to and on the both the absolute and the relative concentrations of the antigen and the antibody, in this case, IFN-γ and the anti-IFN-γ antibody. To be considered capable of inhibiting or modulating the biological activity of IFN-γ as meant herein, an antibody must be able to reverse the inhibition of cell proliferation observed in the presence of IFN-γ, as measured by fluorescence in the A549 assay (Example 6) or a similar assay, by at least about 20%, 40%, 60%, 80%, 85%, 100%, or more when the IFN-γ concentration is within a range, for example, at about $EC_{80}$ or $EC_{90}$, where the effects of an agent that inhibits its biological activity can be readily apparent. An $EC_{80}$, as meant herein, is the amount of IFN-γ required for 80% of the maximal effect of IFN-γ to be observed. If the IFN-γ concentration is well above $EC_{90}$, effects of an inhibiting agent may be less apparent due to the excess of IFN-γ. The concentration of an antibody required to inhibit or modulate the biological activity of IFN-γ can vary widely and may depend upon how tightly the antibody binds to IFN-γ. For example, one molecule or less of an antibody per molecule of IFN-γ may be sufficient to inhibit or modulate biological activity in the A549 assay. In some embodiments, a ratio of IFN-γ antibody of about 2:1, 1:1, 1:2, 1:4, 1:6, 1:8, 1:10, 1:20, 1:40, 1:60, 1:100, or 1:50,000 may be required to inhibit or modulate the biological activity of IFN-γ when the IFN-γ concentration is from about $EC_{50}$ to about $EC_{90}$. Ratios of IFN-γ:antibody between these values are also possible.

In additional embodiments, antibody variants can include antibodies comprising a modified Fc fragment or a modified heavy chain constant region. An Fc fragment, which stands for "fragment that crystallizes," or a heavy chain constant region can be modified by mutation to confer on an antibody altered characteristics. See, for example, Burton and Woof, 1992, *Advances in Immunology* 51: 1-84; Ravetch and Bolland, 2001, *Annu. Rev. Immunol.* 19: 275-90; Shields et al., 2001, *Journal of Biol. Chem.* 276: 6591-6604; Telleman and Junghans, 2000, *Immunology* 100: 245-251; Medesan et al., 1998, *Eur. J. Immunol.* 28: 2092-2100; all of which are incorporated herein by reference). Such mutations can include substitutions, additions, deletions, or any combination thereof, and are typically produced by site-directed mutagenesis using one or more mutagenic oligonucleotide(s) according to methods described herein, as well as according to methods known in the art (see, for example, Maniatis et al., MOLECULAR CLONING: A LABORATORY MANUAL, 3rd Ed., 2001, Cold Spring Harbor, N.Y. and Berger and Kimmel, METHODS IN ENZYMOLOGY, Volume 152, Guide to Molecular Cloning Techniques, 1987, Academic Press, Inc., San Diego, Calif., which are incorporated herein by reference).

In certain embodiments, antibody variants include glycosylation variants wherein the number and/or type of glycosylation site has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid, or attachment to a polypeptide or nucleic acid of a fluorescent marker, a chemiluminescent marker or an enzyme having a detectable activity, or attachment to a polypeptide of biotin moieties that can be detected by labeled avidin (e.g., streptavidin preferably comprising a detectable marker such as a fluorescent marker, a chemiluminescent marker or an enzymatic activity that can be detected, inter alia, by optical or colorimetric methods). In certain embodiments, the label can also be therapeutic. Various methods of labeling polypeptides and glycoproteins are known in the art and may be used advantageously in the methods disclosed herein. Examples of labels for polypeptides include, but are not limited to, the following: radioisotopes or radionuclides (e.g., $^{3}H$, $^{14}C$, $^{15}N$, $^{35}S$, $^{90}Y$, $^{99m}Tc$, $^{111}In$, $^{125}I$, $^{131}I$), fluorescent labels (e.g., fluorescein isothiocyanate or FITC, rhodamine, or lanthanide phosphors), enzymatic labels (e.g., horseradish peroxidase, β-galactosidase, luciferase, alkaline phosphatase), chemiluminescent labels, hapten labels such as biotinyl groups, and predetermined polypeptide epitopes recognized by a secondary reporter (e.g., leucine zipper pair sequences, binding sites for secondary antibodies, metal binding domains, or epitope tags). In certain embodiments, labels are attached by spacer arms (such as $(CH_2)_n$, where n<about 20) of various lengths to reduce potential steric hindrance.

The term "biological sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

The term "pharmaceutical agent or drug" as used herein refers to a chemical compound or composition capable of inducing a desired therapeutic effect when properly administered to a patient.

The term "IFN-γ mediated disease" includes, but is not limited to, inflammatory, infectious, and autoimmune diseases. An "autoimmune disease" as used herein refers to disease states and conditions wherein a patient's immune response is directed toward the patient's own constituents. For example, IFN-γ mediated diseases include, but are not limited to, Acquired Immune Deficiency Syndrome (AIDS), rheumatoid arthritis including juvenile rheumatoid arthritis, inflammatory bowel diseases including ulcerative colitis and Crohn's disease, multiple sclerosis, Addison's disease, diabetes (type I), epididymitis, glomerulonephritis, Graves' disease, Guillain-Barre syndrome, Hashimoto's disease, hemolytic anemia, systemic lupus erythematosus (SLE), lupus nephritis, myasthenia gravis, pemphigus, psoriasis, psoriatic arthritis, atherosclerosis, erythropoietin resistance, graft versus host disease, transplant rejection, autoimmune hepatitis-induced hepatic injury, biliary cirrhosis, alcohol-induced liver injury including alcoholic cirrhosis, rheumatic fever, sarcoidosis, scleroderma, Sjogren's syndrome, spondyloarthropathies including ankylosing spondylitis, thyroiditis, and vasculitis. The term "IFN-gamma mediated disease" also encompasses any medical condition associated with increased levels of IFN-γ or increased sensitivity to IFN-γ.

Treatment of an IFN-γ mediated disease, including an autoimmune disease, encompasses alleviation of at least one symptom of the disorder, a reduction in the severity of the disease, or the delay or prevention of progression to a more serious disease that occurs with some frequency following the treated condition. Treatment need not mean that the disease is totally cured. A useful therapeutic agent needs only to reduce the severity of a disease, reduce the severity of a symptom or symptoms associated with the disease or its treatment, or provide improvement to a patient's quality of life, or delay the onset of a more serious disease that can occur with some frequency following the treated condition. For example, if the disease is a rheumatoid arthritis, a therapeutic agent may decrease swelling of joints, reduce the number of joints affected, or delay or inhibit bone loss. An SLE patient can have symptoms such as skin lesions, fever, weakness, arthritis, lymphadenopathy, pleurisy, pericarditis, and/or anemia, among others. Such symptoms can be assessed by any of a number of conventional techniques including, for example, visual observation, photography, measurement of temperature, grip strength, or joint size, and/or microscopic examination of blood to determine the concentration of red blood cells. The invention encompasses a method of treatment comprising administering to a patient afflicted with a IFN-γ mediated disease an IFN-γ antibody of the invention in an amount and for a time sufficient to induce a sustained improvement over baseline of an indicator that reflects the severity of a particular disorder or the severity of symptoms caused by the disorder or to delay or prevent the onset of a more serious disease that follows the treated condition in some or all cases. The invention does not exclude possible treatment with other therapeutic agents before, after, and/or during treatment with the IFN-γ antibody.

As used herein, "substantially pure" or "substantially purified" means a compound or species that is the predominant species present (i.e., on a molar basis it is more abundant than any other individual species in the composition). In certain embodiments, a substantially purified fraction is a composition wherein the species comprises at least about 50 percent (on a molar basis) of all macromolecular species present. In certain embodiments, a substantially pure composition will comprise more than about 80%, 85%, 90%, 95%, or 99% of all macromolar species present in the composition. In certain embodiments, the species is purified to essential homogeneity (contaminant species cannot be detected in the composition by conventional detection methods) wherein the composition consists essentially of a single macromolecular species.

The term "patient" includes human and animal subjects.

Unless otherwise required by context, singular terms shall include pluralities.

Because IFN-γ is a cytokine with multiple functions, including protecting the body from viral infection and regulating several aspects of the immune response, increased IFN-γ activity can contribute to several pathological conditions. According to certain embodiments of the invention, antibodies directed to IFN-γ may be used to treat IFN-γ mediated diseases, including but not limited to, those mentioned above.

In one aspect of the invention are provided fully human monoclonal antibodies raised against and having biological and immunological specificity for specific binding to human IFN-γ. Variable regions (SEQ ID NO:6, SEQ ID NO:8, SEQ ID NO:10, SEQ ID NO:12, SEQ ID NO:14, SEQ ID NO:16, SEQ ID NO:30, and SEQ ID NO:31) included in such antibodies, complete heavy and light chains of such antibodies (SEQ ID NO:17, SEQ ID NO:18, SEQ ID NO:19, SEQ ID NO:20, SEQ ID NO:21, and SEQ ID NO:22), and antibodies comprising specific CDRs (heavy and light chain CDR1, CDR2, and/or CDR3; SEQ ID NO:34 through SEQ ID NO:44) are encompassed by the invention. Particular embodiments of this aspect of the invention are sequences corresponding to CDR's, specifically from CDR1 through CDR3, of the heavy and light chains provided by the invention. Further, the invention encompasses antibodies comprising a CDR3 sequence disclosed herein (SEQ ID NO:36, SEQ ID NO:37, SEQ ID NO:43, and/or SEQ ID NO:44) that may also contain sequences at least 80%, 85%, 90%, 91%, 92%, 93%, 94%, 95%. 96%, 97%, 98%, or about 99% identical to any of the variable region sequences or complete heavy or light chain sequences disclosed herein, wherein the antibody can inhibit or modulate the biological activity of IFN-γ.

In another aspect the invention provides isolated nucleic acids or polynucleotides encoding the antibodies of the invention. Antibodies of the invention can bind specifically to and/or inhibit or modulate the biological activity of IFN-γ. Specifically encompassed by the invention are polynucleotides comprising nucleotide sequences encoding the amino acid sequences SEQ ID NO:17, SEQ ID NO:18, SEQ ID NO:19, SEQ ID NO:20, SEQ ID NO:21, SEQ ID NO:22, SEQ ID NO:32, SEQ ID NO:33, SEQ ID NO:5, SEQ ID NO:7, SEQ ID NO:9, SEQ ID NO:11, SEQ ID NO:13, SEQ ID NO:15, SEQ ID NO:30, SEQ ID NO:31, and/or sequences that are at least 80%, 85%, 90%, 91%, 92%, 93%, 94%, 95%, 96%, 97%, 98%, or about 99% identical to these sequences, wherein the alignment between the sequences above and the test sequence span at least about 50, 60, 70, 80, 90, or 100 amino acids. The invention further provides polynucleotides comprising SEQ ID NO:45, SEQ ID NO:46, SEQ ID NO:47, and/or SEQ ID NO:48, that encode antibodies that can bind specifically to and/or inhibit or modulate the biological activity of IFN-γ. Further, the invention encompasses polynucleotides that are at least 80%, 85%, 90%, 91%, 92%, 93%, 94%, 95%, 96%, 97%, 98%, or about 99% identical to SEQ ID NO:5, SEQ ID NO:7, SEQ ID NO:9, SEQ ID NO:11, SEQ ID NO:13, SEQ ID NO:15, SEQ ID NO:30, SEQ ID NO:31, SEQ ID NO:17, SEQ ID NO:18, SEQ ID NO:19, SEQ ID NO:20, SEQ ID NO:21, SEQ ID NO:22, SEQ ID NO:32, or SEQ ID NO:33, wherein an antibody encoded in part by each of these polynucleotides can inhibit or modulate the biological activity of and/or bind specifically to IFN-γ and wherein the alignment between the nucleotide sequences named immediately above and the test sequence spans at least about 100, 150, or 200 nucleotides.

Table 2 provides a brief description of the sequences as they relate to their sequence identification numbers.

TABLE 2

BRIEF DESCRIPTION OF THE SEQUENCE LISTINGS

| Sequence Identification Number | Brief Description |
|---|---|
| SEQ ID NO: 1 | Nucleotide sequence encoding the heavy chain constant region of the 1118, 1118*, 1119, 1121, or 1121* antibody |
| SEQ ID NO: 2 | Amino acid sequence of the heavy chain constant region of the 1118, 1118*, 1119, 1121, or 1121* antibody |
| SEQ ID NO: 3 | Nucleotide sequence encoding the light chain constant region of the 1118, 1118*, 1119, 1121, or 1121* antibody |
| SEQ ID NO: 4 | Amino acid sequence of the light chain constant region of the 1118, 1118*, 1119, 1121, or 1121* antibody |
| SEQ ID NO: 5 | Nucleotide sequence encoding the heavy chain variable region of the 1119 antibody |
| SEQ ID NO: 6 | Amino acid sequence of the heavy chain variable region of the 1119 antibody |
| SEQ ID NO: 7 | Nucleotide sequence encoding the light chain variable region of the 1119 antibody |
| SEQ ID NO: 8 | Amino acid sequence of the light chain variable region of the 1119 antibody |
| SEQ ID NO: 9 | Nucleotide sequence encoding the heavy chain variable region of the 1118 antibody |
| SEQ ID NO: 10 | Amino acid sequence of the heavy chain variable region of the 1118 antibody |
| SEQ ID NO: 11 | Nucleotide sequence encoding the light chain variable region of the 1118 or 1118* antibody |
| SEQ ID NO: 12 | Amino acid sequence of the light chain variable region of the 1118 or 1118* antibody |

TABLE 2-continued

BRIEF DESCRIPTION OF THE SEQUENCE LISTINGS

| Sequence Identification Number | Brief Description |
|---|---|
| SEQ ID NO: 13 | Nucleotide sequence encoding the heavy chain variable region of the 1121 or 1121* antibody |
| SEQ ID NO: 14 | Amino acid sequence of the heavy chain variable region of the 1121 or 1121* antibody |
| SEQ ID NO: 15 | Nucleotide sequence encoding the light chain variable region of the 1121 antibody |
| SEQ ID NO: 16 | Amino acid sequence of the light chain variable region of the 1121 antibody |
| SEQ ID NO: 17 | Amino acid sequence of the entire heavy chain of the 1119 antibody |
| SEQ ID NO: 18 | Amino acid sequence of the entire light chain of the 1119 antibody |
| SEQ ID NO: 19 | Amino acid sequence of the entire heavy chain of the 1118 antibody |
| SEQ ID NO: 20 | Amino acid sequence of the entire light chain of the 1118 or 1118* antibody |
| SEQ ID NO: 21 | Amino acid sequence of the entire heavy chain of the 1121 or 1121* antibody |
| SEQ ID NO: 22 | Amino acid sequence of the entire light chain of the 1121 antibody |
| SEQ ID NO: 23 | Nucleotide sequence of a PCR primer |
| SEQ ID NO: 24 | Nucleotide sequence of a PCR primer |
| SEQ ID NO: 25 | Nucleotide sequence of a PCR primer |
| SEQ ID NO: 26 | Nucleotide sequence of a PCR primer |
| SEQ ID NO: 27 | Nucleotide sequence of a PCR primer |
| SEQ ID NO: 28 | Nucleotide sequence of a PCR primer |
| SEQ ID NO: 29 | Nucleotide sequence of a PCR primer |
| SEQ ID NO: 30 | Amino acid sequence of the heavy chain variable region of 1118* antibody |
| SEQ ID NO: 31 | Amino acid sequence of the light chain variable region of 1121* antibody |
| SEQ ID NO: 32 | Amino acid sequence of the entire heavy chain of the 1118* antibody |
| SEQ ID NO: 33 | Amino acid sequence of the entire light chain of the 1121* antibody |
| SEQ ID NO: 34 | Amino acid sequence of the heavy chain CDR1 of the 1119, 1118, 1118*, 1121, or 1121* antibody |
| SEQ ID NO: 35 | Amino acid sequence of the heavy chain CDR2 of the 1119, 1118, 1118*, 1121, or 1121* antibody |
| SEQ ID NO: 36 | Amino acid sequence of the heavy chain CDR3 of the 1119 antibody |
| SEQ ID NO: 37 | Amino acid sequence of the heavy chain CDR3 of the 1118, 1118*, 1121, or 1121* antibody |
| SEQ ID NO: 38 | Amino acid sequence of the light chain CDR1 of the 1119 or 1121 antibody |
| SEQ ID NO: 39 | Amino acid sequence of the light chain CDR1 of the 1118 or 1118* antibody |
| SEQ ID NO: 40 | Amino acid sequence of the light chain CDR1 of the 1121* antibody |
| SEQ ID NO: 41 | Amino acid sequence of the light chain CDR2 of the 1119, 1118, 1118*, or 1121 antibody |
| SEQ ID NO: 42 | Amino acid sequence of the light chain CDR2 of the 1121* antibody |
| SEQ ID NO: 43 | Amino acid sequence of the light chain CDR3 of the 1119, 1118, 1118*, or 1121 antibody |
| SEQ ID NO: 44 | Amino acid sequence of the light chain CDR3 of the 1121* antibody |
| SEQ ID NO: 45 | Nucleotide sequence encoding the heavy chain CDR3 of the 1119 antibody |
| SEQ ID NO: 46 | Nucleotide sequence encoding the heavy chain CDR3 of the 1118, 1118*, 1121, or 1121* antibody |
| SEQ ID NO: 47 | Nucleotide sequence encoding the light chain CDR3 of the 1118, 1118*, 1119, or 1121 antibody |
| SEQ ID NO: 48 | Amino acid sequence immediately preceding a heavy chain CDR1 |
| SEQ ID NO: 49 | Amino acid sequence that may immediately precede a heavy chain CDR2 |
| SEQ ID NO: 50 | Amino acid sequence that almost always follows a heavy chain CDR3 |
| SEQ ID NO: 51 | Amino acid sequence that usually follows a light chain CDR3 |
| SEQ ID NO: 52 | Amino acid sequence of a signal sequence |
| SEQ ID NO: 53 | Amino acid sequence of a signal sequence |
| SEQ ID NO: 54 | Amino acid sequence of a signal sequence |
| SEQ ID NO: 55 | Amino acid sequence of a signal sequence |
| SEQ ID NO: 56 | Nucleotide sequence of the heavy chain variable region of 1118* antibody |
| SEQ ID NO: 57 | Nucleotide sequence of the light chain variable region of 1121* antibody |

In yet another aspect the invention provides hybridoma cells and cell lines that express the immunoglobulin molecules and antibodies of the invention, optionally monoclonal antibodies. In a further aspect, a hybridoma cell or a cell from a cell line that expresses and/or secretes an immunoglobulin molecule or antibody of the invention can be implanted in a patient, whereby an antibody of the invention or immunologically functional immunoglobulin fragment thereof is expressed and/or secreted in the patient, thereby inhibiting or modulating IFN-γ activity.

The invention also provides biologically and immunologically purified preparations of antibodies, preferably monoclonal antibodies raised against and having biological and immunological specificity for binding specifically to human IFN-γ.

The ability to clone and reconstruct megabase-sized human loci in yeast artificial chromosomes (YACs) and to introduce them into the mouse germline permits development of an advantageous approach to elucidating the functional components of very large or crudely mapped loci as well as generating useful models of human disease. Furthermore, the utilization of such technology for substitution of mouse loci with their human equivalents produces unique insights into the expression and regulation of human gene products during development, their communication with other systems, and their involvement in disease induction and progression.

An important practical application of such a strategy is the alteration of the mouse humoral immune system by the introduction of human immunoglobulin (Ig) loci into mice in which the endogenous Ig genes have been inactivated. International Application No. WO 93/12227. This system offers the opportunity to study mechanisms underlying programmed expression and assembly of antibodies as well as their role in B-cell development. Furthermore, such a strategy provides a source for production of fully human monoclonal antibodies (MAbs). Fully human MAbs are expected to minimize the immunogenic and allergic responses intrinsic to mouse or mouse-derived MAbs, and to thereby increase the efficacy and safety of the administered antibodies. Fully human antibodies can be used in the treatment of chronic and recurring human diseases, such as osteoarthritis, rheumatoid arthritis, and other inflammatory conditions, the treatment thereof requiring repeated antibody administration. Thus, one particular advantage of the anti-IFN-γ antibodies of the invention is that the antibodies are fully human and can be administered to patients in a non-acute manner while minimizing adverse reactions commonly associated with mouse anti-human antibodies or other previously described non-fully human antibodies or non-human antibodies from non-human species.

Using methods set forth herein, one skilled in the art can engineer mouse strains deficient in mouse antibody production with large fragments of the human Ig loci so that such mice produce human antibodies in the absence of mouse antibodies. Large human Ig fragments may preserve the large variable gene diversity as well as the proper regulation of antibody production and expression. By exploiting the mouse cellular machinery for antibody diversification and selection and the lack of immunological tolerance to human proteins, the reproduced human antibody repertoire in these mouse strains yields high affinity antibodies against any antigen of interest, including human antigens. Using the hybridoma technology, antigen-specific human MAbs with the desired specificity may be produced and selected.

In certain embodiments, the skilled artisan can use constant regions from species other than human along with the human variable region(s) in such mice to produce chimeric antibodies.

Naturally Occurring Antibody Structure

Most naturally occurring antibody structural units typically comprise a tetramer. Each such tetramer typically is composed of two identical pairs of polypeptide chains, each pair having one full-length "light" chain (typically having a molecular weight of about 25 kDa) and one full-length "heavy" chain (typically having a molecular weight of about 50-70 kDa). The amino-terminal portion of each light and heavy chain typically includes a variable region of about 100 to 110 or more amino acids that typically is responsible for antigen recognition. The carboxy-terminal portion of each chain typically defines a constant region responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., FUNDAMENTAL IMMUNOLOGY, Ch. 7, $2^{nd}$ ed., (Paul, W., ed.), 1989, Raven Press, N.Y. (incorporated by reference in its entirety for all purposes). The variable regions of each light/heavy chain pair typically form the antigen-binding site.

Some naturally-occurring antibodies, which have been found in camels and llamas, are dimers consisting of two heavy chains and include no light chains. Muldermans et al., 2001, J. Biotechnol. 74:277-302; Desmyter et al., 2001, J. Biol. Chem. 276:26285-90. The invention encompasses dimeric antibodies consisting of two heavy chains that can bind to and/or inhibit the biological activity of IFN-γ. A crystallographic study of a camel antibody has revealed that the heavy chain CDR3, which is 19 amino acids long, forms a surface that interacts with the antigen and covers the two other hypervariable regions. Desmyter et al., supra. Thus, CDR3 is important for antigen binding in dimeric camel antibodies, as well as in the more typical tetrameric antibodies.

The variable regions typically exhibit the same general structure of relatively conserved framework regions (FR) joined by three hypervariable regions, also called complementarity determining regions or CDRs. The CDRs from the two chains of each pair are typically embedded within the framework regions, which may enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat et al., as explained in more detail below. Kabat et al., Sequences of Proteins of Immunological Interest (1991, National Institutes of Health, Bethesda, Md.); see also Chothia & Lesk, 1987, J. Mol. Biol. 196:901-917; Chothia et al., 1989, Nature 342:878-883. CDRs constitute the major surface contact points for antigen binding. See e.g. Chothia and Lesk, supra. Further, CDR3 of the light chain and, especially, CDR3 of the heavy chain may constitute the most important determinants in antigen binding within the light and heavy chain variable regions. See e.g. Chothia and Lesk, supra; Desiderio et al. (2001), J. Mol. Biol. 310: 603-15; Xu and Davis (2000), Immunity 13(1): 37-45; Desmyter et al. (2001), J. Biol. Chem. 276(28): 26285-90; and Muyldermans (2001), J. Biotechnol. 74(4): 277-302. In some antibodies, the heavy chain CDR3 appears to constitute the major area of contact between the antigen and the antibody. Desmyter et al, supra. In vitro selection schemes in which CDR3 alone is varied can be used to vary the binding properties of an antibody. Muyldermans, supra; Desiderio, supra.

CDRs can be located in a heavy chain variable region sequence in the following way. $CDR_1$ starts at approximately residue 31 of the mature antibody and is usually about 5-7 amino acids long, and it is almost always preceded by a Cys-Xxx-Xxx-Xxx-Xxx-Xxx-Xxx-Xxx-Xxx (SEQ ID NO: 48) (where "Xxx" is any amino acid). The residue following the heavy chain CDR1 is almost always a tryptophan, often a Typ-Val, a Trp-Ile, or a Trp-Ala. Fourteen amino acids are almost always between the last residue in CDR1 and the first in CDR2, and CDR2 typically contains 16 to 19 amino acids. CDR2 may be immediately preceded by Leu-Glu-Trp-Ile-Gly (SEQ ID NO: 49) and may be immediately followed by Lys/Arg-Leu/IleNal/Phe/Thr/Ala-Thr/Ser/Ile/Ala. Other amino acids may precede or follow CDR2. Thirty-two amino acids are almost always between the last residue in CDR2 and the first in CDR3, and CDR3 can be from about 3 to 25 residues long. A Cys-Xxx-Xxx almost always immediately precedes CDR3, and a Trp-Gly-Xxx-Gly (SEQ ID NO: 50) almost always follows CDR3.

Light chain CDRs can be located in a light chain sequence in the following way. CDR1 starts at approximately residue 24 of the mature antibody and is usually about 10 to 17 residues long. It is almost always preceded by a Cys. There are almost always 15 amino acids between the last residue of CDR1 and the first residue of CDR2, and CDR2 is almost always 7 residues long. CDR2 is typically preceded by Ile-Tyr, Val-Tyr, Ile-Lys, or Ile-Phe. There are almost always 32 residues between the light chain CDR2 and CDR3, and CDR3 is usually about 7 to 10 amino acids long. CDR3 is almost always preceded by Cys and usually followed by Phe-Gly-Xxx-Gly (SEQ ID NO: 51).

One of skill in the art will realize that the lengths of framework regions surrounding the CDRs can contain insertions or deletions that make their length differ from what is typical. As meant herein, the length of heavy chain framework regions fall within the following ranges: FR1, 0 to 41 amino acids; FR2, 5 to 24 amino acids; FR3, 13 to 42 amino acids; and FR4, 0 to 21 amino acids. Further, the invention contemplates that the lengths of light chain framework regions fall within the following ranges: FR1, 6 to 35 amino acids; FR2, 4 to 25 amino acids; FR3, 2 to 42 amino acids; and FR4, 0 to 23 amino acids.

Naturally occurring antibodies typically include a signal sequence, which directs the antibody into the cellular pathway for protein secretion and which is not present in the mature antibody. A polynucleotide encoding an antibody of the invention may encode a naturally occurring signal sequence or a heterologous signal sequence as described below.

In Vitro Maturation of Antibodies

Antibodies can be matured in vitro to produce antibodies with altered properties, such as a higher affinity for an antigen or a lower dissociation constant. Variation of only residues within the CDRs, particularly the CDR3s, can result in altered antibodies that bind to the same antigen, but with greater affinity. See e.g. Schier et al., 1996, J. Mol. Biol. 263:551-67; Yang et al., 1995, J. Mol. Biol. 254:392-403. The invention encompasses antibodies created by a variety of in vitro selection schemes, such as affinity maturation and/or chain shuffling (Kang et al., 1991, Proc. Natl. Acad. Sci. 88:11120-23), or DNA shuffling (Stemmer, 1994, Nature 370:389-391), by which antibodies may be selected to have advantageous properties. In many schemes, a known antibody is randomized at certain positions, often within the CDRs, in vitro and subjected to a selection process whereby antibodies with desired properties, such as increased affinity for a certain antigen, can be isolated. See e.g. van den Beucken et al., 2001, J. Mol. Biol. 310:591-601; Desiderio et al., 2001, J. Mol. Biol. 310: 603-15; Yang et al., 1995, J. Mol. Biol. 254:392-403; Schier et al., 1996, J. Mol. Biol. 263:551-67. Typically, such mutated antibodies may comprise several altered residues in one or more CDRs, depending on the design of the mutagenesis and selection steps. See e.g. van den Beucken et al., supra.

Bispecific or Bifunctional Antibodies

A bispecific or bifunctional antibody typically is an artificial hybrid antibody having two different heavy chain/light chain pairs and two different binding sites. Bispecific antibodies may be produced by a variety of methods including, but not limited to, fusion of hybridomas or linking of F(ab') fragments. See, e.g., Songsivilai & Lachmann, 1990, Clin. Exp. Immunol. 79: 315-321; Kostelny et al., 1992, J. Immunol. 148:1547-1553.

Preparation of Antibodies

The invention provides antibodies that bind specifically to human IFN-γ. These antibodies can be produced by immunization with full-length IFN-γ or fragments thereof. The antibodies of the invention can be polyclonal or monoclonal and/or may be recombinant antibodies. In certain embodiments, fully human antibodies of the invention are prepared, for example, by immunization of transgenic animals capable of producing human antibodies (see, for example, International Patent Application, Publication WO 93/12227).

The CDRs of the light chain and heavy chain variable regions of anti-IFN-γ antibodies of the invention can be grafted to framework regions (FRs) from the same, or another, species. In certain embodiments, the CDRs of the light chain and heavy chain variable regions of anti-IFN-γ antibody may be grafted to consensus human FRs to create a "humanized" antibody. Such humanized antibodies are encompassed by the instant invention. To create consensus human FRs, FRs from several human heavy chain or light chain amino acid sequences are aligned to identify a consensus amino acid sequence. The FRs of the anti-IFN-γ antibody heavy chain or light chain can be replaced with the FRs from a different heavy chain or light chain. Rare amino acids in the FRs of the heavy and light chains of anti-IFN-γ antibody typically are not replaced, while the rest of the FR amino acids can be replaced. Rare amino acids are specific amino acids that are in positions in which they are not usually found in FRs. The grafted variable regions from anti-IFN-γ antibodies of the invention can be used with a constant region that is different from an original constant region of an anti-IFN-γ antibody. Alternatively, the grafted variable regions are part of a single chain Fv antibody. CDR grafting is described, e.g., in U.S. Pat. Nos. 6,180,370, 5,693,762, 5,693,761, 5,585,089, and 5,530,101, which are hereby incorporated by reference for any purpose.

Antibodies of the invention can be prepared using transgenic mice that have a substantial portion of the human antibody producing locus inserted in antibody-producing cells of the mice, and that are further engineered to be deficient in producing endogenous, murine, antibodies. Such mice are capable of producing human immunoglobulin molecules and antibodies and do not produce or produce substantially reduced amounts of murine immunoglobulin molecules and antibodies. Technologies utilized for achieving this result are disclosed in the patents, applications, and references disclosed in the specification herein. In certain embodiments, the skilled worker may employ methods as disclosed in International Patent Application Publication No. WO 98/24893, which is hereby incorporated by reference for any purpose. See also Mendez et al., 1997, Nature Genetics 15:146-156, which is hereby incorporated by reference for any purpose.

The monoclonal antibodies (mAbs) of the invention can be produced by a variety of techniques, including conventional monoclonal antibody methodology, e.g., the standard somatic cell hybridization technique of Kohler and Milstein (1975, Nature 256:495). Although somatic cell hybridization procedures are preferred, in principle, other techniques for producing monoclonal antibodies can be employed, e.g., viral or oncogenic transformation of B-lymphocytes.

One possible animal system for preparing hybridomas is the mouse. Hybridoma production in the mouse is very well established, and immunization protocols and techniques for isolation of immunized splenocytes for fusion are well known in the art. Fusion partners (e.g., murine myeloma cells) and fusion procedures are also known.

In some embodiments fully human monoclonal antibodies directed against IFN-γ, optionally human IFN-γ, can be generated using transgenic mice carrying parts of the human immune system rather than the mouse system. These transgenic mice, referred to herein as "HuMab" mice, contain a human immunoglobulin gene minilocus that encodes unrearranged human heavy (μ and γ) and .kappa. light chain immunoglobulin sequences, together with targeted mutations that inactivate the endogenous μ and .kappa. chain loci (Lonberg et al., 1994, Nature 368:856-859). Accordingly, the mice exhibit reduced expression of mouse IgM or .kappa. and in response to immunization, the introduced human heavy chain and light chain transgenes undergo class switching and somatic mutation to generate high affinity human IgG .kappa. monoclonal antibodies (Lonberg et al., supra.; Lonberg and Huszar, 1995, Intern. Rev. Immunol. 13:65-93; Harding and Lonberg, 1995, Ann. N.Y. Acad. Sci. 764:536-546). The preparation of HuMab mice is described in detail in Taylor et al., 1992, Nucleic Acids Res. 20:6287-6295; Chen et al., 1993, International Immunology 5:647-656; Tuaillon et al., 1994, J. Immunol. 152:2912-2920; Lonberg et al., 1994, Nature 368:856-859; Lonberg, 1994, Handbook of Exp. Pharmacology 113:49-101; Taylor et al., 1994, International Immunology 6:579-591; Lonberg & Huszar, 1995, Intern. Rev. Immunol. 13:65-93; Harding & Lonberg, 1995, Ann. N.Y. Acad. Sci. 764:536-546; Fishwild et al., 1996, Nature Biotechnology 14:845-851, the contents of all of which are hereby incorporated by reference in their entirety. See further U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, as well as U.S. Pat. No. 5,545,807 to Surani et al.; International Patent Application Publication Nos. WO 93/1227, published Jun. 24, 1993; WO 92/22646, published Dec. 23, 1992; and WO 92/03918, published Mar. 19, 1992, the disclosures of all of which are hereby incorporated by reference in their entirety. Alternatively, the HCo7 and HCo12 transgenic mice strains described in the Examples below can be used to generate human anti-IFN-γ antibodies.

In these embodiments, the antibodies of the invention bind specifically to IFN-γ with an equilibrium dissociation constant ($K_D$) of less than $10^{-7}$ M, $10^{-8}$ M, $10^{-9}$ M, or $10^{-10}$ M. In certain embodiments of the invention, the antibodies bind to IFN-γ with a $K_D$ of between approximately $10^8$ M and $10^{12}$ M.

In preferred embodiments, the antibodies of the invention are of the IgG1, IgG2, or IgG4 isotype. The antibodies can be of the IgG1 isotype. In other embodiments, the antibodies of the invention are of the IgM, IgA, IgE, or IgD isotype. In preferred embodiments of the invention, the antibodies comprise a human kappa light chain and a human IgG1 heavy chain. Expression of antibodies of the invention comprising an IgG1 heavy chain constant region is described in the Examples below. In particular embodiments, the variable regions of the antibodies are ligated to a constant region other than the constant region for the IgG1 isotype. In certain embodiments, the antibodies of the invention have been cloned for expression in mammalian cells.

In certain embodiments, conservative modifications to the heavy chains and light chains of anti-IFN-γ antibody (and corresponding modifications to the encoding nucleotides) will produce anti-IFN-γ antibodies having functional and chemical characteristics similar to those of anti-IFN-γ antibody. In contrast, substantial modifications in the functional and/or chemical characteristics of anti-IFN-γ antibody may be accomplished by selecting substitutions in the amino acid sequence of the heavy and light chains that differ significantly in their effect on maintaining (a) the structure of the molecular backbone in the area of the substitution, for example, as a β sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis."

Desired amino acid substitutions (whether conservative or non-conservative) can be determined by those skilled in the art at the time such substitutions are desired. In certain embodiments, amino acid substitutions can be used to identify important residues of anti-IFN-γ antibody, or to increase or decrease the affinity of the anti-IFN-γ antibodies described herein.

In alternative embodiments, antibodies of the invention can be expressed in cell lines other than hybridoma cell lines. In these embodiments, sequences encoding particular antibodies can be used for transformation of a suitable mammalian host cell. According to these embodiments, transformation can be achieved using any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (all of which are hereby incorporated herein by reference for any purpose). Generally, the transformation procedure used may depend upon the host to be transformed. Methods for introducing heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Nucleic acid molecules (or polynucleotides) encoding the amino acid sequence of a heavy chain constant region, a heavy chain variable region, a light chain constant region, or a light chain variable region of an anti-IFN-γ antibody of the invention are encompassed by the invention. Such polynucleotides can be inserted into an appropriate expression vector using standard ligation techniques. In a preferred embodiment, a polynucleotide encoding the anti-IFN-γ antibody heavy chain or light chain constant region is appended to the downstream end of a polynucleotide encoding the appropriate variable region and is ligated into an expression vector. The vector is typically selected to be functional in the particular host cell employed (i.e., the vector is compatible with the host cell machinery such that amplification of the gene and/or expression of the gene can occur). For a review of expression vectors, see METH. ENZ. 185 (Goeddel, ed.), 1990, Academic Press.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the anti-IFN-γ antibody polypeptide coding sequence; the oligonucleotide sequence encodes polyHis (such as hexaHis), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of the IFN-γ antibody from the host cell. Affinity purification can be accomplished, for example, by column chromatography using antibodies against the tag as an affinity matrix. Optionally, the tag can subsequently be removed from the purified anti-IFN-γ antibody polypeptide by various means such as using certain peptidases for cleavage.

Flanking sequences may be homologous (i.e., from the same species and/or strain as the host cell), heterologous (ie., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagene® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Preferred selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antibody that binds to IFN-γ polypeptide. As a result, increased quantities of a polypeptide such as an anti-IFN-γ antibody are synthesized from the amplified DNA.

A ribosome-binding site is usually necessary for translation initiation of mRNA and is characterized by a Shine-Dalgamo sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the invention will typically contain a promoter that is recognized by the host organism and operably linked to the molecule encoding the anti-IFN-γ antibody. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known. A suitable promoter is operably linked to the DNA encoding heavy chain or light chain comprising an anti-IFN-γ antibody of the invention by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, Nature 290:304-10); CMV promoter (Thomsen et al., 1984, Proc. Natl. Acad. USA 81:659-663); the promoter contained in the 3' long terminal repeat of Rous sarcoma virus (Yamamoto, et al., 1980, Cell 22:787-97); herpes thymidine kinase promoter (Wagner et al., 1981, Proc. Natl. Acad. Sci. U.S.A. 78:144445); promoter and regulatory sequences from the metallothionine gene (Brinster et al., 1982, Nature 296: 39-42); and prokaryotic promoters such as the beta-lactamase promoter (Villa-Kamaroff et al., 1978, Proc. Natl. Acad. Sci. U.S.A., 75:3727-31); or the tac promoter (DeBoer et al., 1983, Proc. Natl. Acad. Sci. U.S.A., 80:21-25). Also of interest are the following animal transcriptional control regions, which exhibit tissue specificity and have been utilized in transgenic animals: the elastase I gene control region that is active in pancreatic acinar cells (Swift et al., 1984, Cell 38:63946; Ornitz et al., 1986, Cold Spring Harbor Symp. Quant. Biol. 50:399409 (1986); MacDonald, 1987, Hepatology 7:425-515); the insulin gene control region that is active in pancreatic beta cells (Hanahan, 1985, Nature 315:115-22); the immunoglobulin gene control region that is active in lymphoid cells (Grosschedl et al., 1984, Cell 38:647-58; Adames et al., 1985, Nature 318:533-38; Alexander et al., 1987, Mol. Cell. Biol, 7:1436-44); the mouse mammary tumor virus control region that is active in testicular, breast, lymphoid and mast cells (Leder et al., 1986, Cell 45:485-95); the albumin gene control region that is active in liver (Pinkert et al., 1987, Genes and Devel. 1:268-76); the alpha-feto-protein gene control region that is active in liver (Krumlauf et al., 1985, Mol. Cell. Biol., 5:1639-48; Hammer et al., 1987, Science 235:53-58); the alpha 1-antitrypsin gene control region that is active in liver (Kelsey et al., 1987, Genes and Devel. 1:161-71); the beta-globin gene control region that is active in myeloid cells (Mogram et al., 1985, Nature 315: 33840; Kollias et al., 1986, Cell 46:89-94); the myelin basic protein gene control region that is active in oligodendrocyte cells in the brain (Readhead et al., 1987, Cell 48:703-12); the myosin light chain-2 gene control region that is active in skeletal muscle (Sani, 1985, Nature 314:283-86); and the gonadotropic releasing hormone gene control region that is active in the hypothalamus (Mason et al., 1986, Science 234: 1372-78).

An enhancer sequence may be inserted into the vector to increase transcription of DNA encoding light chain or heavy chain comprising an anti-IFN-γ antibody of the invention by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyorna enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter.

A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al. (1984, Nature 312: 768); the interleukin-4 receptor signal peptide described in EP Patent No. 0 367 566; the type I interleukin-1 receptor signal peptide described in U.S. Pat. No. 4,968,607; the type II interleukin-1 receptor signal peptide described in EP Patent No. 0 460 846; the signal sequence of human IgK (which is METDTLLLWVLLLWVPGSTG; SEQ ID NO: 52); the signal sequence of human growth hormone (which is MATGSRTSLLLAFGLLCLPWLQEGSA; SEQ ID NO: 53); and the human signal sequences MGSTAILALLLAVLQGVCA (SEQ ID NO: 54) and METPAQLLFLLLLWLPDTTG (SEQ ID NO: 55), which were encoded by cDNAs encoding the heavy and light chains isolated in Example 3.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy chain comprising an anti-IFN-γ antibody has been inserted into the proper site of the vector, the completed vector may be inserted into a suitable host cell for amplification and/or polypeptide expression. The transformation of an expression vector for an anti-IFN-γ antibody into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., supra.

A host cell, when cultured under appropriate conditions, synthesizes an anti-IFN-γ antibody that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and constitutively produce antibodies with IFN-γ binding properties. In another embodiment, a cell line from the B cell lineage that does not make its own antibody but has a capacity to make and secrete a heterologous antibody can be selected.

Antibodies of the invention are useful for detecting IFN-γ in biological samples and identification of cells or tissues that produce IFN-γ protein. Antibodies of the invention that specifically bind to IFN-γ may be useful in treatment of IFN-γ mediated diseases. Said antibodies can be used in binding assays to detect IFN-γ and to inhibit IFN-γ from forming a complex with IFN-γ receptors. Said antibodies that bind to IFN-γ and block interaction with other binding compounds may have therapeutic use in modulating IFN-γ mediated diseases. In preferred embodiments, antibodies to IFN-γ may block IFN-γ binding to its receptor, which may result in disruption of the IFN-γ induced signal transduction cascade.

In some embodiments, the invention provides pharmaceutical compositions comprising a therapeutically effective amount of one or a plurality of the antibodies of the invention together with a pharmaceutically acceptable diluent, carrier, solubilizer, emulsifier, preservative, and/or adjuvant. Preferably, acceptable formulation materials are nontoxic to recipients at the dosages and concentrations employed. In preferred embodiments, pharmaceutical compositions comprising a therapeutically effective amount of anti-IFN-γ antibodies are provided.

In certain embodiments, acceptable formulation materials preferably are nontoxic to recipients at the dosages and concentrations employed.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See REMINGTON'S PHARMACEUTICAL SCIENCES, $18^{th}$ Edition, (A. R. Gennaro, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antibodies of the invention.

In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In preferred embodiments, pharmaceutical compositions comprise Tris buffer of about pH 7.0-8.5, or acetate buffer of about pH 4.0-5.5, and may further include sorbitol or a suitable substitute therefor. In certain embodiments of the invention, anti-IFN-γ antibody compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the anti-IFN-γ antibody product may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired anti-IFN-γ antibody in a pharmaceutically acceptable vehicle. A particularly suitable vehicle for parenteral injection is sterile distilled water in which the anti-IFN-γ antibody is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antibody molecule.

Pharmaceutical compositions of the invention can be formulated for inhalation. In these embodiments, anti-IFN-γ antibodies are advantageously formulated as a dry, inhalable powder. In preferred embodiments, anti-IFN-γ antibody inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins.

It is also contemplated that formulations can be administered orally. Anti-IFN-γ antibodies that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the anti-IFN-γ antibody. Diluents, flavorings, low melting point waxes, vegetable oils, lubricants, suspending agents, tablet disintegrating agents, and binders may also be employed.

A pharmaceutical composition of the invention is preferably provided to comprise an effective quantity of one or a plurality of anti-IFN-γ antibodies in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving anti-IFN-γ antibodies in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g. films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, Biopolymers 22:547-556), poly(2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., supra) or poly-D(−)-3-hydroxybutyric acid (European Patent Application Publication No. EP 133,988). Sustained release compositions may also include liposomes that can be prepared by any of several methods known in the art. See e.g., Eppstein et al., 1985, Proc. Natl. Acad. Sci. USA 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration.

The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The therapeutically effective amount of an anti-IFN-γ antibody-containing pharmaceutical composition to be employed will depend, for example, upon the therapeutic context and objectives. One skilled in the art will appreciate that the appropriate dosage levels for treatment will vary depending, in part, upon the molecule delivered, the indication for which the anti-IFN-γ antibody is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 μg/kg to up to about 30 mg/kg or more, depending on the factors mentioned above. In preferred embodiments, the dosage may range from 0.1 μg/kg up to about 30 mg/kg, optionally from 1 μg/kg up to about 30 mg/kg or from 10 μg/kg up to about 5 mg/kg.

Dosing frequency will depend upon the pharmacokinetic parameters of the particular anti-IFN-γ antibody in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data. In certain embodiments, the antibodies of the invention can be administered to patients throughout an extended time period. Chronic administration of an antibody of the invention minimizes the adverse immune or allergic response commonly associated with antibodies that are raised against a human antigen in a non-human animal, for example, a non-fully human antibody or non-human antibody produced in a non-human species.

The route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also may be desirable to use anti-IFN-γ antibody pharmaceutical compositions according to the invention ex vivo. In such instances, cells, tissues or organs that have been removed from the patient are exposed to anti-IFN-γ antibody pharmaceutical compositions after which the cells, tissues and/or organs are subsequently implanted back into the patient.

In particular, anti-IFN-γ antibodies can be delivered by implanting certain cells that have been genetically engineered, using methods such as those described herein, to express and secrete the polypeptide. In certain embodiments, such cells may be animal or human cells, and may be autologous, heterologous, or xenogeneic. In certain embodiments, the cells may be immortalized. In other embodiments, in order to decrease the chance of an immunological response, the cells may be encapsulated to avoid infiltration of surrounding tissues. In further embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

EXAMPLES

The following examples, including the experiments conducted and results achieved are provided for illustrative purposes only and are not to be construed as limiting the invention.

Example 1

Generation of Human IFNγ Protein from CHO Cells

The full-length human IFN-γ cDNA was amplified by PCR (under standard conditions) using human spleen Marathon-Ready cDNA (Clontech) as a template. The sequence was subcloned into the pDSR.alpha.2 plasmid. DH10B (*Escherichia coli*) cells were transformed with the pDSR.alpha.2 plasmid. DNA was prepared using standard techniques, and CHO cells were transfected by the calcium phosphate method (Speciality Media, Inc.). A high-expressing cell line clone was used to generate serum-free conditioned media.

CHO cell conditioned media containing human IFN-γ (hu-IFN-γ was concentrated, dialyzed, and purified through several chromatography steps. The first step was Q-HP (Pharmacia) chromatography using a standard NaCl gradient to separate highly glycosylated from unglycosylated hu-IFN-γ forms. The Q-HP pool was further purified through wheat germ agglutinin chromatography (EY Laboratories). The purified material was separated by SDS-polyacrylamide gel electrophoresis (SDS-PAGE) and analyzed by Coomassie-blue and silver-staining. The purified material was greater than 95% pure as determined by both Coomassie-blue and silver-stained SDS-PAGE. The material was also assayed by the gel-clot method (*Limulus* Amebocyte Lysate), indicating a low endotoxin level. The identity of hu-IFN-γ was confirmed by Western blotting using anti-AF-285 NA antibody from R & D Systems. The final protein concentration was determined from absorbance ($A_{280}$) using the extinction coefficient method, where $A_{280}$ reading/extinction coefficient=concentration in g/L (extinction coefficient=0.66).

Example 2

Production of Human Monoclonal Antibodies Against IFN-γ

Transgenic HuMab Mice

Fully human monoclonal antibodies to IFN-γ were prepared using HCo7, HCo12, and HCo7+HCo12 strains of transgenic mice, each of which expressed human antibody genes. In each of these strains, the endogenous mouse kappa light chain gene had been homozygously disrupted as described in Chen et al. (1993, EMBO J. 12:811-820), and the endogenous mouse heavy chain gene had been homozygously disrupted as described in Example 1 of International Patent Application Publication No. WO 01/09187 (incorporated by reference). Each strain carried a human kappa light chain transgene, KCo5, as described in Fishwild et al. (1996, Nature Biotechnology 14:845-851). The HCo7 strain carries the HCo7 human heavy chain transgene as described in U.S. Pat. Nos. 5,545,806, 5,625,825, and 5,545,807 (incorporated by reference). The HCo12 strain carried the HCo12 human heavy chain transgene as described in Example 2 of International Patent Application Publication No. WO 01/09187 (incorporated by reference). The HCo7+HCo12 strain carried both the HCo7 and the HCo12 heavy chain transgenes and was hemizygous for each transgene. All of these strains are referred to herein as HuMab mice.

HuMab Immunizations:

To generate fully human monoclonal antibodies to IFN-γ, HuMab mice were immunized with purified recombinant human IFN-γ derived from *E. coli* or CHO cells as antigen. General immunization schemes for HuMab mice are described in Lonberg et al. (1994, Nature 368:856-859; Fishwild et al., supra., and International Patent Application Publication No. WO 98/24884, the teachings of each of which are incorporated by reference). Mice were 6-16 weeks of age upon the first infusion of antigen. A purified recombinant preparation (25-100 μg) of IFN-γ antigen (e.g., purified from transfected *E. coli* or CHO cells expressing IFN-γ) was used to immunize the HuMab mice intraperitoneally (IP) or subcutaneously (Sc).

Immunizations of HuMab transgenic mice were achieved using antigen in complete Freund's adjuvant and two injections, followed by 2-4 weeks IP immunization (up to a total of 9 immunizations) with the antigen in incomplete Freund's adjuvant. Several dozen mice were immunized for each antigen (human IFN-γ produced in either *E. coli* or CHO cells). A total of 91 mice of the HCo7, HCo12, and HCo7+HCo12 strains were immunized with IFN-γ. The immune response was monitored by retroorbital bleeds.

To select HuMab mice producing antibodies that bound IFN-γ, sera from immunized mice was tested by ELISA as described by Fishwild et al. supra. Briefly, microtiter plates were coated with purified recombinant IFN-γ from CHO cells or *E. coli* at 1-2 μL/mL in PBS and 50 μL/well incubated at 4° C. overnight, then blocked with 200 μL/well of 5% chicken serum in PBS/Tween (0.05%). Dilutions of plasma from IFN-γ-immunized mice were added to each well and incubated for 1-2 hours at ambient temperature. The plates were washed with PBS/Tween and then incubated with a goat-anti-human IgG Fc-specific polyclonal reagent conjugated to horseradish peroxidase (HRP) for 1 hour at room temperature. Plates were washed with PBS/Tween and incubated with a goat anti-human IgG Fc-specific polyclonal reagent conjugated to horseradish peroxidase (HRP) for 1 hour at room temperature. After washing, the plates were developed with ABTS substrate (Sigma Chemical Co., St. Louis, Mo., Catalog No. A-1888, 0.22 mg/mL) and analyzed spectrophotometrically by determining optical density (OD) at wavelengths from 415-495 nm. Mice with sufficient titers of anti-IFN-γ human immunoglobulin were used to produce monoclonal antibodies as described below.

Generation of Hybridomas Producing Human Monoclonal Antibodies to IFN-γ.

Mice were prepared for monoclonal antibody production by boosting with antigen intravenously 2 days before sacrifice, and spleens were removed thereafter. The mouse splenocytes were isolated from the HuMab mice and fused with PEG to a mouse myeloma cell line using standard protocols. Typically, 10-20 fusions for each antigen were performed.

Briefly, single cell suspensions of splenic lymphocytes from immunized mice were fused to one-fourth the number of P3X63-Ag8.653 nonsecreting mouse myeloma cells (ATCC, Accession No. CRL 1580) with 50% PEG (Sigma). Cells were plated at approximately $1\times10^5$/well in flat bottom microtiter plates, followed by about a two week incubation in selective medium containing 10% fetal bovine serum, 10% P388D1-(ATCC, Accession No. CRL TIB-63) conditioned medium, 3-5% ORIGEN® Hybridoma Cloning Factor (IGEN), a partially purified hybridoma growth medium supplement derived from medium used to culture a murine macrophage-like cell line, in DMEM (Mediatech, Catalog No. CRL 10013, with high glucose, L-glutamine, and sodium pyruvate) plus 5 mM HEPES, 0.055 mM 2-mercaptoethanol, 50 mg/mL gentamycin, and 1×HAT (Sigma, Catalog No. CRL P-7185). After 1-2 weeks, cells were cultured in medium in which the HAT was replaced with HT.

The resulting hybridomas were screened for the production of antigen-specific antibodies. Individual wells were screened by ELISA (described above) for human anti-IFN-γ monoclonal IgG antibodies. Once extensive hybridoma growth occurred, medium was monitored, usually after 10-14 days. Antibody secreting hybridomas were replated, screened again and, if still positive for human IgG, anti-IFN-γ monoclonal antibodies were subcloned at least twice by limiting dilution. The stable subclones were then cultured in vitro to generate small amounts of antibody in tissue culture medium for purification and characterization.

Selection of Human Monoclonal Antibodies that Bind to IFN-γ

An ELISA assay as described above was used to screen for hybridomas that showed positive reactivity with IFN-γ immunogen. Hybridomas secreting a monoclonal antibody that bound with high avidity to IFN-γ were subcloned and further characterized. One clone from each hybridoma, which retained the reactivity of parent cells (as determined by ELISA), was chosen for making a 5-10 vial cell bank stored in liquid nitrogen.

An isotype-specific ELISA was performed to determine the isotype of the monoclonal antibodies produced as disclosed herein. In these experiments, microtiter plate wells were coated with 50 µL/well of a solution of 1 µg/mL of mouse anti-human kappa light chain in PBS and incubated at 4° C. overnight. After blocking with 5% chicken serum, the plates were reacted with supernatant from each tested monoclonal antibody and a purified isotype control. Plates were incubated at ambient temperature for 1-2 hours. The wells were then reacted with either human IgG1 or IgG3-specific horseradish peroxidase-conjugated goat anti-human polyclonal antisera, and plates were developed and analyzed as described above.

Monoclonal antibodies purified from the hybridoma supernatants that showed significant binding to IFN-γ as detected by ELISA were further tested for biological activity using a variety of bioassays as described below. The antibodies selected were designated 1119, 1121, 1118*, 1121*, and 1118.

Example 3

Cloning the Anti-IFN-γ Antibody Heavy and Light Chains

The hybridomas expressing IFN-γ binding monoclonal antibodies 1119, 1121, 1118*, 1121*, and 1118 identified in Example 2 above were used as sources to isolate total RNA using TRIzol® reagent (Invitrogen), a monophasic solution of phenol and guanidine isothiocyanate suitable for isolating total RNA, DNA, and protein. First strand cDNA was synthesized using a random primer with an extension adapter (5'-GGC CGG ATA GGC CTC CAN NNN NNT-3') (SEQ ID NO:23) and a 5' RACE (rapid amplification of cDNA ends) preparative assay was performed using the GENERACER™ Kit (Invitrogen), a kit for rapid amplification of cDNA ends (RACE) with improved efficiency, according to instructions from the manufacturer. For preparing complete light chain-encoding cDNA, the forward primer was the GENERACER™ nested primer, and the reverse primer was 5'-GGG GTC AGG CTG GAA CTG AGG-3' (SEQ ID NO:24). The reverse primer was designed to recognize a conserved region of the cDNA sequence found in the 3' untranslated region of human kappa chains. For preparing cDNA encoding the variable region of the heavy chains, the forward primer was the GENERACER™ nested primer and the reverse primer was 5'-TGA GGA CGC TGA CCA CAC G-3' (SEQ ID NO:25), which was designed to recognize a conserved region in the coding sequence in the Fc region of human IgG chains. RACE products were cloned into pCR4-TOPO (Invitrogen), and the sequences were determined. Consensus sequences were used to design primers for full-length antibody chain PCR amplification.

For preparing cDNA encoding anti-IFN-γ kappa light chain, the 5' PCR primer encoded the amino terminus of the signal sequence, an XbaI restriction enzyme site, and an optimized Kozak sequence (5'-ACA ACA AAG CTT CTA GAC CAC CAT GGA AAC CCC AGC TCA GCT TCT CTT-3'; SEQ ID NO:26). The 3' primer encoded the carboxyl terminus and termination codon, as well as a SalI restriction site (5'-CTT GTC GAC TCA ACA CTC TCC CCT GTT GAA GCT-3'; SEQ ID NO:27). The resulting PCR product fragment was purified, digested with XbaI and SalI, and then gel isolated and ligated into the mammalian expression vector pDSR.alpha.9 (see International Application, Publication No. WO 90/14363, which is herein incorporated by reference for any purpose).

For preparing cDNA encoding anti-IFN-γ heavy chain the 5' PCR primer encoded the amino terminus of the signal sequence, an XbaI restriction enzyme site, and an optimized Kozak sequence (5'-CAG CAG AAG CTT CTA GAC CAC CAT GGG GTC AAC CGC CAT CCT CG-3'; SEQ ID NO:28). The 3' primer encoded the carboxyl end of the variable region, including a naturally occurring sense strand BsmBI site (5'-CTT GGT GGA GGC ACT AGA GAC GGT GAC CAG GGT GCC ACG GCC-3'; SEQ ID NO:29). The resulting product was purified, digested with XbaI and BsmBI, gel isolated and ligated into the pDSR.alpha.19 vector containing the human IgG1 constant region.

Example 4

Expression of Anti-IFN-γ Antibodies in Chinese Hamster Ovary (CHO) Cells

Stable expression of the 1119 anti-IFN-γ mAb was achieved by co-transfection of 1119-heavy chain/pDSR.alpha.19 and 1119-kappa chain/pDSR.alpha.19 plasmids into dihydrofolate reductase deficient (DHFR⁻), serum-free adapted Chinese hamster ovary (CHO) cells using a calcium phosphate method. Transfected cells were selected in medium containing dialyzed serum but not containing hypoxanthine-thymidine to ensure the growth of cells expressing the DHFR enzyme. Transfected clones were screened using assays such as ELISA in order to detect the expression of 1119 anti-IFN-γ mAb in the conditioned medium. The 1119-expressing cell lines were subjected to methotrexate amplification. The highest expressing clones upon amplification were selected for single cell cloning and creation of cell banks Any recombinant anti-IFN-γ antibody of the invention can be generated in Chinese hamster ovary cells deficient in DHFR using the same protocol as described above for the 1119 MAb. The DNA sequences encoding the complete heavy chain or light chain of each anti-IFN-γ antibody of the invention are cloned into expression vectors. CHO cells deficient in DHFR are co-transfected with an expression vector capable of expressing a complete heavy chain and an expression vector expressing the complete light chain of the appropriate anti-IFN-γ antibody. For example, to generate the 1118 antibody, cells are co-transfected with a vector capable of expressing a complete heavy chain comprising the amino acid sequence as set forth in SEQ ID NO: 19 and a vector capable of expressing a complete light chain comprising the amino acid sequence set forth in SEQ ID NO: 20. To generate the 1121 antibody, cells are co-transfected with a vector capable of expressing a complete heavy chain comprising the amino acid sequence as set forth in SEQ ID NO: 21 and a vector capable of expressing a complete light chain comprising the amino acid sequence set forth in SEQ ID NO: 22. To generate the 1118* antibody, cells are co-transfected with a vector capable of expressing a complete heavy chain comprising the amino acid sequence as set forth in SEQ ID NO: 32 and a vector capable of expressing a complete light chain comprising the amino acid sequence set forth in SEQ ID NO: 20. To generate the 1121* antibody, cells are co-transfected with a vector capable of expressing a complete heavy chain comprising the amino acid sequence as set forth in SEQ ID NO: 21 and a vector capable of expressing a complete light chain comprising the amino acid sequence set forth in SEQ ID NO: 33. Table 3 summarizes the complete heavy and complete light chains for the various IFN-γ antibodies.

TABLE 3

| Antibody | Heavy Chain Variable Region + Heavy Chain Constant Region | Complete Heavy Chain |
|---|---|---|
| 1119 | SEQ ID NO: 6 + SEQ ID NO: 2 | SEQ ID NO: 17 |
| 1118 | SEQ ID NO: 10 + SEQ ID NO: 2 | SEQ ID NO: 19 |
| 1121 | SEQ ID NO: 14 + SEQ ID NO: 2 | SEQ ID NO: 21 |
| 1121* | SEQ ID NO: 14 + SEQ ID NO: 2 | SEQ ID NO: 21 |
| 1118* | SEQ ID NO: 30 + SEQ ID NO: 2 | SEQ ID NO: 32 |

| Antibody | Light Chain Variable Region + Light Chain Constant Region | Complete Light Chain |
|---|---|---|
| 1119 | SEQ ID NO: 8 + SEQ ID NO: 4 | SEQ ID NO: 18 |
| 1118 | SEQ ID NO: 12 + SEQ ID NO: 4 | SEQ ID NO: 20 |
| 1121 | SEQ ID NO: 16 + SEQ ID NO: 4 | SEQ ID NO: 22 |
| 1121* | SEQ ID NO: 31 + SEQ ID NO: 4 | SEQ ID NO: 33 |
| 1118* | SEQ ID NO: 12 + SEQ ID NO: 4 | SEQ ID NO: 20 |

Example 5

Production of Anti-IFN-γ Antibody

The 1119 antibody was produced by expression in a clonal line of CHO cells that expressed it. For the production run, cells from a single vial were thawed into serum-free cell culture media. The cells were grown initially in a 250 mL shake flask, then in spinner flasks, and finally in stainless steel reactors of increasing scale up to a 2000 L bioreactor. Production was carried out in a 2000 L bioreactor using a fed batch culture, in which a nutrient feed containing concentrated media components is added to maintain cell growth and culture viability. Production lasted for approximately two weeks, during which time the 1119 antibody was constitutively produced by the cells and secreted into the cell culture medium.

The production reactor was controlled at a predetermined pH, temperature, and dissolved oxygen level. The pH was controlled by carbon dioxide gas and sodium carbonate addition. Dissolved oxygen was controlled by air, nitrogen, and oxygen gas flows.

At the end of production, the cell broth was fed into a disk stack centrifuge, and the culture supernatant was separated from the cells. The concentrate is further clarified through a depth filter followed by a 0.2 µm filter. The clarified conditioned media was then concentrated by tangential flow ultrafiltration. The conditioned media was concentrated 15- to 30-fold. The resulting concentrated conditioned medium was then processed to purify the antibody it contains, but it may be frozen for purification at a later date. Any of the other antibodies described herein could be produced in a similar fashion.

Example 6

Characterizing the Activity of Anti-IFN-γ Antibodies

Since IFN-γ has a large number of biological effects, several different bioassays were used to compare the potency of various IFN-γ antibodies. The A549 assay described below was used for the primary screen with candidates selected for further analysis based on their performance in the assay. Selected candidates included the 1119, 1118, and 1121 antibodies.

A549 Bioassay

One of the established properties of IFN-γ is its anti-proliferative effect on a variety of cell populations. See e.g. Aune and Pogue, 1989, J. Clin. Invest. 84:863-75. The human lung cell line A549 has been used frequently in publications describing the bioactivity of IFN-γ. See e.g. Aune and Pogue, supra; Hill et al., 1993, Immunology 79:236-40. In general, the activity of an inhibitor is tested at a concentration of a stimulating substance that falls within a part of the dose-response curve where a small change in dose will result in a change in response. One of skill in the art will realize that if an excessive dose of the stimulating substance is used, a very large dose of an inhibitor may be required to observe a change in response. Commonly used concentrations for a stimulating substance are $EC_{80}$ and $EC_{90}$ (the concentrations at which 80% or 90%, respectively, of the maximum response is achieved).

An IFN-γ dose-response curve was generated to determine the $EC_{90}$ for the lung epithelial carcinoma cell line A549 (~30 pM). In subsequent experiments, different concentrations of purified antibodies were mixed with a fixed dose of IFN-γ (30 pM), and the ability of the antibodies to inhibit the biological activity of the anti-proliferative effect of IFN-γ was determined. The assay was performed for 5 days, and proliferation was measured by determining fluorescence generated by the reduction of ALAMARBLUE™ (AccuMed International, Inc., Chicago, Ill.), a dye used to indicate cell growth, by metabolically active, i.e., proliferating, cells. See e.g., de Fries and Mitsuhashi, 1995, J. Clin. Lab. Analysis 9(2):89-95; Ahmed et al., 1994, J. Immunol. Methods 170(2):211-24.

As shown in FIG. 9, the 1119 antibody was the most potent antibody with an $IC_{50}$ (concentration at which 50% inhibition of the effect of IFN-γ was achieved) of 14 pM, followed by 1121 (46 pM), and 1118 (97 pM).

HLA DR Bioassay

Another established property of IFN-γ is its ability to upregulate the expression of MHC Class I and Class II genes in a variety of cell types. This activity may be particularly relevant to lupus nephritis (Yokoyama et al., 1992, Kidney Int. 42:755-63). The THP-1 human monocytic cell line has been used frequently in publications describing this bioactivity of IFN-γ. An IFN-γ dose-response curve was generated to determine the $EC_{80}$ for the particular THP-1 cell line used in this experiment (~21 pM). In subsequent experiments, different concentrations of purified antibodies were mixed with a fixed dose of IFN-γ (21 pM) and the ability of the antibodies to neutralize or inhibit the IFN-γ-induced upregulation of HLA DR expression on the cell surface was determined. The assay was performed for 24 hours, and the measured endpoint was mean fluorescence intensity as determined by FACS analysis to detect binding of a FITC-labeled anti-HLA DR antibody to the cells.

Figure 10:
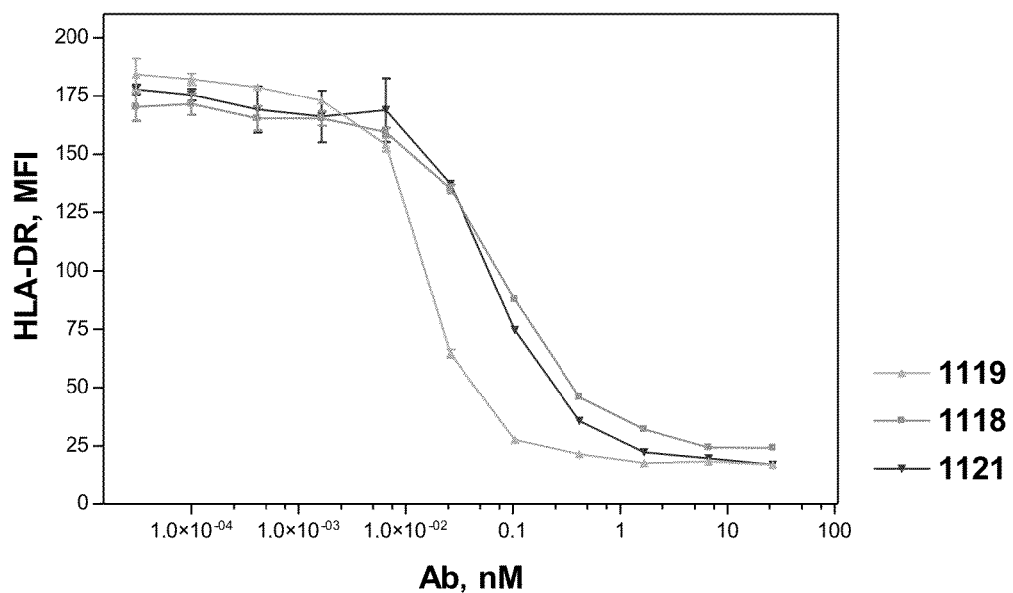

As shown in FIG. 10, the 1119 antibody was the most potent antibody with an $IC_{50}$ of 14 pM, followed by 1121 (60 pM), and 1118 (86 pM).

Whole Blood Bioassay

Figure 11:
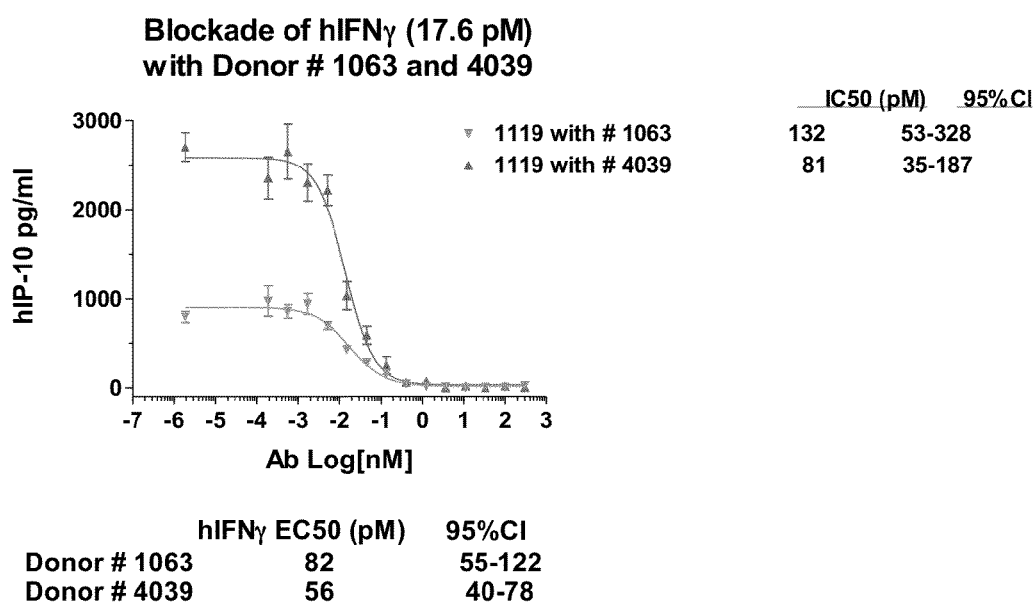
Figure 14:
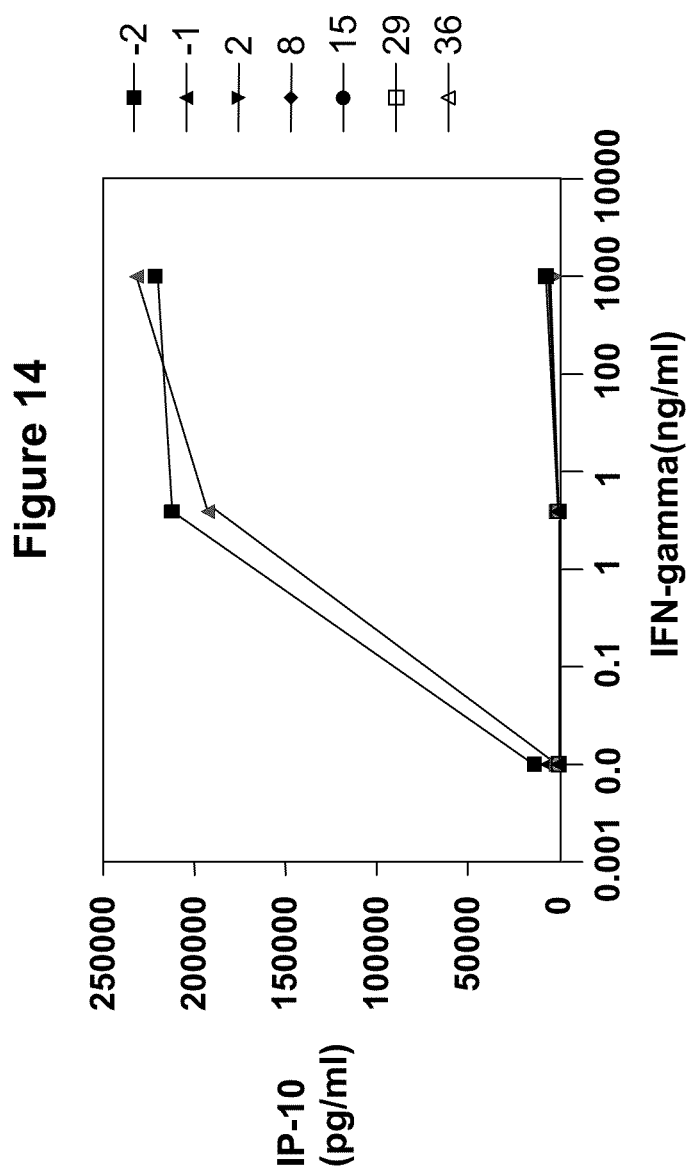
FIG. 14 shows production of IP-10 in response to IFN-γ by whole blood taken from a chimpanzee at 2 or 1 week(s) prior to (lines labeled "−2" and "−1" in FIG. 14) or 2, 8, 15, 29, or 36 days after (lines labeled "2," "8," "15," "29," or "36" in FIG. 14) the start of a course of 3 injections of anti-IFN-γ antibody, which occurred once per week.
Figure 15:
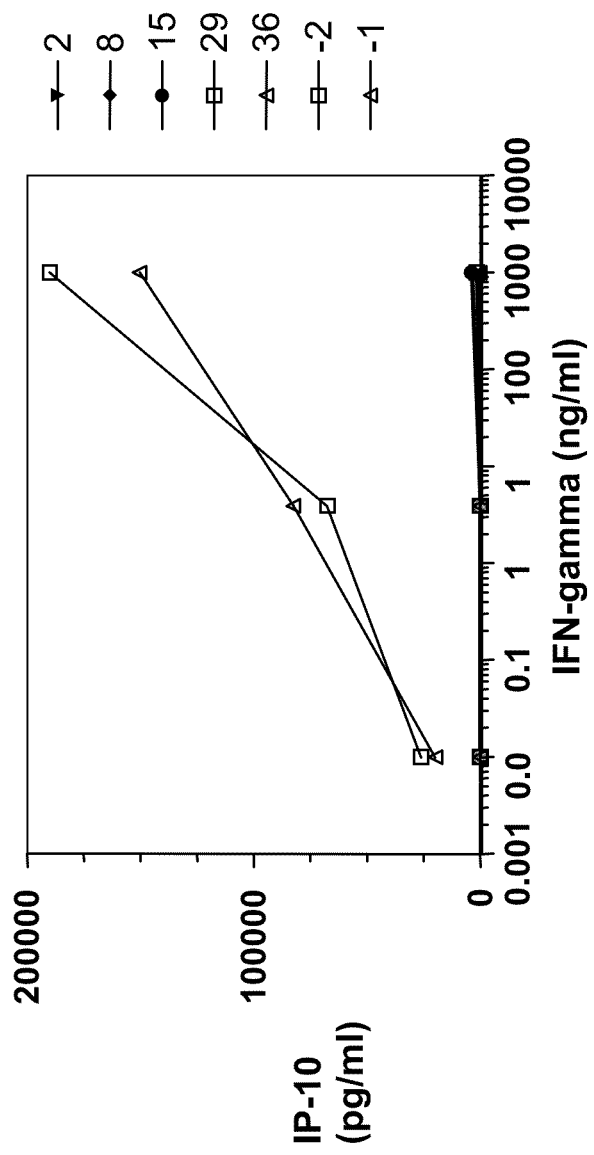
FIG. 15 is similar to FIG. 14 except that the blood of a different chimpanzee was used.

A human whole blood assay was developed based on published observations that IFN-γ upregulates the production of the IP-10 chemokine in several different cell lines. This activity may be particularly relevant to lupus nephritis (Narumi et al., 2000, Cytokine 12:1561-1565). Whole blood from a number of normal human donors was tested for the ability of IFN-γ to increase IP-10 production. An IFN-γ dose-response curve was generated to determine the $EC_{50}$ for individual donors. As expected, some variation was observed between donors. In general, donors were used that appeared to reproducibly display an $EC_{50}$ of 50-100 pM. Whole blood was mixed with a fixed concentration of IFN-γ and different concentrations of antibodies, incubated for 18.5 hours and then IP-10 levels determined by ELISA. Representative results from a whole blood assay for two different donors are shown in FIG. 11. The $IC_{50}$s from these two donors were 17 and 14 pM. To date, one donor has been identified with spontaneously elevated IP-10 levels in the whole blood assay without need for the addition of exogenous IFN-γ. The anti-IFN-γ antibodies were capable of blocking this spontaneous production of IP-10 presumably by blocking the endogenously produced IFN-γ.

Biochemical Assays

Binding kinetics for several of the antibodies to IFN-γ were measured by BIAcore analysis. Initial results suggested that the antibodies had off-rates that approached the limitations for reliable measurements on the BIACORE™ (Pharmacia Biosensor AB Corporation, Uppsala, Sweden), an apparatus that uses surface plasmon resonance to measure binding between molecules. Accordingly, an equilibrium-binding assay was developed and used. A fixed amount of antibody was incubated with various concentrations of IFN-γ for greater than 5 hours in order to reach equilibrium and then contacted with IFN-γ coupled beads for a very brief time, and the amount of free antibody that bound to the beads was measured in a KINEXA™ machine (Sapidyne Instruments Inc., Boise, Id.), a fluorescence based immunoassay instrument. The lowest equilibrium dissociation constant obtained, ~24 pM, was with the 1119 antibody.

Example 7

Species Cross-Reactivity

The antibodies described above were tested for their ability to neutralize or inhibit recombinant IFN-γ proteins from several different species. The mouse IFN-γ protein was purchased commercially, while the human, cynomolgus monkey and chimpanzee IFN-γ proteins were cloned and expressed in conventional mammalian expression systems such as human 293 cells. The human, cynomolgus, and chimpanzee IFN-γ proteins were all active in the previously described A549 assay while the mouse protein was not active in this assay. The mouse protein was active in a RAW 264.7 cell-line based assay, which was essentially identical to the A549 assay described previously except for the substitution of the mouse cell line. RAW 264.7 is a mouse monocytic macrophage cell line and can be obtained from, for example, the American Type Culture Collection. As shown in Table 4, all three antibodies were able to neutralize human and chimpanzee IFN-γ, while none of the three were able to neutralize or inhibit the biological activity of IFN-γ from either cynomolgus or mouse.

TABLE 4

| Antibody | Human | Chimp. | Cyno. | Mouse |
| --- | --- | --- | --- | --- |
| 1118 | Yes | Yes | No | No |
| 1119 | Yes | Yes | No | No |
| 1121 | Yes | Yes | No | No |

Example 8

Identification of an Epitope for Anti-IFN-γ Antibodies

A comparison of the amino acid sequences of mature human and cynomolgus IFN-γ indicated that there were nine amino acid differences between them at positions 19, 20, 31, 34, 65, 77, 103, 110, and 126 in the human IFN-γ sequence. Human and chimpanzee IFN-γ sequences are disclosed in Thakur and Landolfi (1999), Molecular Immunology 36: 1107-15, The cynomolgus monkey IFN-γ sequence is disclosed in Tatsumi and Sata (1997), Int. Arch. Allergy Immunol. 114(3): 229-36; and the murine IFN-γ sequence is disclosed in, e.g., National Center for Biotechnology Information (NCBI) Accession No. NP_032363. Site-directed mutagenesis using a commercially available kit was used to substitute individually each of the divergent human amino acids within the human IFN-γ with the corresponding amino acid from the cynomolgus protein. Each substituted IFN-γ was named "huIFN-γ" followed by the symbol for the amino acid used to replace the amino acid present in the human IFN-γ sequence and the position in the mature human IFN-γ sequence at which the substitution occurred. For example, "huIFNγD19" represents a version of IFN-γ identical to human IFN-γ except at position 19, where an aspartic acid replaces the histidine normally occupying this position. Similar experiments were done starting with the cynomolgus monkey IFN-γ and substituting each divergent amino acid with the amino acid present in human IFN-γ. For example, "cynoIFNγL103" represents a version of IFN-γ identical to cynomolgus monkey IFN-γ except at position 103, where a leucine replaces the serine normally occupying this position. See Tables 5 and 6. These mutant proteins were expressed in a conventional mammalian expression system such as the human 293 cells. All the mutant IFN-γ proteins retained activity as determined in the A549 assay. The 1119 antibody was tested for its ability to neutralize or inhibit the biological activity of the various mutant IFN-γ proteins, as determined using an A549 bioassay. The ability of the 1119 antibody to neutralize or inhibit human IFN-γ anti-proliferative activity was determined by measuring fluorescence as described above, and this was used as a baseline for comparing the ability of the 1119 antibody to neutralize the activity of each of the variant forms of IFN-γ. For the constructs that started with human IFN-γ, inhibition of IFN-γ activity was measured as a percentage, where maximal level of fluorescence observed in the presence of the human IFN-γ and the 1119 antibody (due to reduction of ALAMARBLUE™ by proliferating cells) was set to 100%, and the maximal levels measured in the presence of each of the altered forms of IFN-γ plus the 1119 antibody were compared to this. Alternatively, for the constructs that started with cynomolgus monkey IFN-γ, inhibition was scored qualitatively based on the observed fluorescence.

As summarized in Table 5, the 1119 antibody was able to neutralize or inhibit the biological activity of human IFN-γ and all the substitution mutants of human IFN-γ except for huIFNγD19 and huIFNγP20. As in the previous example, the cynomolgus IFN-γ protein was also not inhibited by the 1119 antibody. This analysis indicates that residues 19 and 20 are particularly important for the interaction between the 1119 antibody and IFN-γ and may serve as points of contact between the 1119 antibody and human IFN-γ.

TABLE 5

| IFN-γ | % Neutralization by 1119 |
|---|---|
| Human IFN-γ | 100 |
| Cynomolgus IFN-γ | 0 |
| huIFN-γD19 | 0 |
| huIFN-γP20 | 0 |
| huIFN-γD31 | 103 |
| huIFN-γR34 | 109 |
| huIFN-γR65 | 109 |
| huIFN-γI77 | 108 |
| huIFN-γS103 | 102 |
| huIFN-γV110 | 103 |
| huIFN-γI126 | 109 |

Table 6 shows that an altered version of the cynomolgus monkey IFN-γ comprising substitutions making the cynomolgus IFNγ sequence match the human sequence at positions 19 and 20 was not neutralized by the 1119 antibody. However, versions of the cynomolgus monkey IFNγ having human sequence substitutions at positions 19, 20, and 65, or 19, 20, and 103 were neutralized by the 1119 antibody, as were versions containing substitutions in addition to either of these.

TABLE 6

| Construct | Neutralization by 1119 |
|---|---|
| human IFNγ | yes |
| cyno IFNγ | no |
| cyno IFNγH19/S20 | no |
| cyno IFNγS65 | no |
| cyno IFNγL103 | no |
| cyno IFNγS65/L103 | no |
| cyno IFNγH19/S20/S65 | yes |
| cyno IFNγH19/S20/L103 | yes |
| cyno IFNγH19/S20/L103/I110 | yes |
| cyno IFNγH19/S20/S65/L103/I110 | yes |

Example 9

Biological Activity of Anti-IFN-γ Antibody Upon Administration to Chimpanzees The 1119 antibody was administered to two chimpanzees at a dose of 20 mg/kg every week for three weeks. Blood was drawn from the chimpanzees either two (−2) or one week (−1) before administration of antibody, and further blood was drawn at 2, 8, 15, 29, and 36 days after administration of the first dose of antibody. A chimpanzee whole blood assay was performed on the drawn blood using essentially the same method used in the human whole blood assay described in Example 6, the key distinction being that the antibody was not added to the whole blood exogenously but was administered previously in vivo to the chimpanzees. IFN-γ was added to the blood at various concentrations (0.01 ng/ml, 3.9 ng/ml, or 1 ug/ml), the blood was incubated at 37° C. for 20-24 hours, and then IP-10 production was measured by bead-based ELISA.

As can be seen in FIGS. 14 and 15, blood drawn from animals prior to antibody dosing responded to IFN-γ with a concentration dependent increase in IP-10 production. In contrast, blood drawn after antibody administration did not respond to any of the concentrations of IFN-γ tested with an increase in IP-10 production. These data indicate that the antibody retained the ability to neutralize IFN-γ, even after administration in vivo. Further, the amount of IFN-γ added to these cultures greatly exceeded the endogenous levels of IFN-γ in the chimpanzees, suggesting that the administered antibody would be capable of neutralizing endogenous IFN-γ in vivo.

It should be understood that the foregoing disclosure emphasizes certain specific embodiments of the invention and that all modifications or alternatives equivalent thereto are within the spirit and scope of the invention as set forth in the appended claims. All references cited herein are incorporated by reference in their entirety.

What is claimed is:

1. A method for treating a patient having systemic lupus erythematosus comprising administering to the patient a human anti-human IFNγ antibody, wherein the antibody comprises a heavy chain CDR1 comprising the amino acid sequence of SEQ ID NO:34, a heavy chain CDR2 comprising the amino acid sequence of SEQ ID NO:35, a heavy chain CDR3 comprising the amino acid sequence of SEQ ID NO:36, a light chain CDR1 comprising the amino acid sequence of SEQ ID NO:38, a light chain CDR2 comprising the amino acid sequence of SEQ ID NO:41, and a light chain CDR3 comprising the amino acid sequence of SEQ ID NO:43.

2. The method of claim 1, wherein the antibody comprises the amino acid sequence of SEQ ID NO:6.

3. The method of claim 1, wherein the patient has lupus nephritis.

4. The method of claim 3, wherein the antibody comprises the amino acid sequence of SEQ ID NO:6.

5. The method of claim 2, wherein the antibody comprises the amino acid sequence of SEQ ID NO:8.

6. The method of claim 4, wherein the antibody comprises the amino acid sequence of SEQ ID NO:8.

7. The method of claim 1, wherein the antibody comprises the amino acid sequence of SEQ ID NO:8.

8. The method of claim 3, wherein the antibody comprises SEQ ID NO:8.

9. A method for treating a patient having an inflammatory bowel disease comprising administering to the patient a human anti-human IFNγ antibody, wherein the antibody comprises a heavy chain CDR1 comprising the amino acid sequence of SEQ ID NO:34, a heavy chain CDR2 comprising the amino acid sequence of SEQ ID NO:35, a heavy chain CDR3 comprising the amino acid sequence of SEQ ID NO:36, a light chain CDR1 comprising the amino acid sequence of SEQ ID NO:38, a light chain CDR2 comprising the amino acid sequence of SEQ ID NO:41, and a light chain CDR3 comprising the amino acid sequence of SEQ ID NO:43.

10. The method of claim 9, wherein the antibody comprises the amino acid sequence of SEQ ID NO:6.

11. The method of claim 9, wherein the patient has Crohn's disease.

12. The method of claim 11, wherein the antibody comprises the amino acid sequence of SEQ ID NO:6.

13. The method of claim 10, wherein the antibody comprises the amino acid sequence of SEQ ID NO:8.

14. The method of claim 11, wherein the antibody comprises the amino acid sequence of SEQ ID NO:8.

15. The method of claim 9, wherein the antibody comprises the amino acid sequence of SEQ ID NO:8.

16. The method of claim 12, wherein the antibody comprises SEQ ID NO:8.

17. A method for treating a patient having psoriasis comprising administering to the patient a human anti-human IFNγ antibody, wherein the antibody comprises a heavy chain CDR1 comprising the amino acid sequence of SEQ ID NO:34, a heavy chain CDR2 comprising the amino acid sequence of SEQ ID NO:35, a heavy chain CDR3 comprising the amino acid sequence of SEQ ID NO:36, a light chain CDR1 comprising the amino acid sequence of SEQ ID NO:38, a light chain CDR2 comprising the amino acid sequence of SEQ ID NO:41, and a light chain CDR3 comprising the amino acid sequence of SEQ ID NO:43.

18. The method of claim 17, wherein the antibody comprises the amino acid sequence of SEQ ID NO:6.

19. The method of claim 17, wherein the antibody comprises the amino acid sequence of SEQ ID NO:8.

20. The method of claim 18, wherein the antibody comprises the amino acid sequence of SEQ ID NO:8.

* * * * *

SEQUENCE LISTING

```
<160> NUMBER OF SEQ ID NOS: 57

<210> SEQ ID NO 1
<211> LENGTH: 990
<212> TYPE: DNA
<213> ORGANISM: Homo Sapiens

<400> SEQUENCE: 1
gcctccacca agggcccatc ggtcttcccc ctggcaccct cctccaagag cacctctggg     60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
```

-continued

```
tacatctgca acgtgaatca caagcccagc aacaccaagg tggacaagaa agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctat agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990
```

<210> SEQ ID NO 2
<211> LENGTH: 330
<212> TYPE: PRT
<213> ORGANISM: Homo sapiens

<400> SEQUENCE: 2

```
Ala Ser Thr Lys Gly Pro Ser Val Phe Pro Leu Ala Pro Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
```

```
            245                 250                 255
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 3
<211> LENGTH: 321
<212> TYPE: DNA
<213> ORGANISM: Homo Sapiens

<400> SEQUENCE: 3
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321

<210> SEQ ID NO 4
<211> LENGTH: 107
<212> TYPE: PRT
<213> ORGANISM: Homo sapiens

<400> SEQUENCE: 4

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 5
<211> LENGTH: 351
<212> TYPE: DNA
<213> ORGANISM: Homo Sapiens

<400> SEQUENCE: 5
gaggtgcagc tggtacagtc tggagcagag gtgaaaaagc ccggggagtc tctgaagatc      60
tcctgtaagg gttctggata caactttacc agctactgga tcggctgggt gcgccagatg     120
cccgggaaag gcctggagtt gatggggatc atctatcctg gtgactctga taccagatac     180
```

```
agcccgtcct tccaaggcca ggtcaccatc tcagccgaca agtccatcag caccgcctac    240
ctgcagtgga gcagcctgaa ggcctcggac accgccatgt attactgtgg ttcggggagc    300 tactttact  tcgatctctg gggccgtggc accctggtca ccgtctctag t             351
```

<210> SEQ ID NO 6
<211> LENGTH: 117
<212> TYPE: PRT
<213> ORGANISM: Homo sapiens

<400> SEQUENCE: 6

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Ser Tyr
            20                  25                  30

Trp Ile Gly Trp Val Arg Gln Met Pro Gly Lys Gly Leu Glu Leu Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Ser Gly Ser Tyr Phe Tyr Phe Asp Leu Trp Gly Arg Gly Thr Leu
            100                 105                 110

Val Thr Val Ser Ser
        115
```

<210> SEQ ID NO 7
<211> LENGTH: 324
<212> TYPE: DNA
<213> ORGANISM: Homo Sapiens

<400> SEQUENCE: 7

```
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatatat ggtgcatcca gcagggccac tggcatccca    180
gacaggttca gtggcagtgg gtctgggaca gacttcactc tcaccatcag cagactggag    240
cctgaagatt ttgcagtgta ttactgtcag cggtctggtg gctcatcatt cactttcggc    300
cctgggacca aagtggatat caaa                                           324
```

<210> SEQ ID NO 8
<211> LENGTH: 108
<212> TYPE: PRT
<213> ORGANISM: Homo sapiens

<400> SEQUENCE: 8

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Arg Ser Gly Gly Ser Ser
                85                  90                  95

Phe Thr Phe Gly Pro Gly Thr Lys Val Asp Ile Lys
            100                 105
```

<210> SEQ ID NO 9
<211> LENGTH: 351
<212> TYPE: DNA
<213> ORGANISM: Homo Sapiens

<400> SEQUENCE: 9

```
gaggtgcagc tggtgcagtc tggagcagag gtgaaaaagc ccggggagtc tctgaagatc    60
tcctgtaagg gttctggata cagctttacc agctactgga tcggctgggt gcgccagatg   120
cccgggaaag gcctggagtg gatggggatc atctatcctg gtgactctga taccagatac   180
agcccgtcct ccaaggcca ggtcaccatc tcagccgaca gtccatcag caccgcctac    240 ctgcagtgga gcagcctgaa ggcctcggac accgccatgt attactgtgg ttcggggagc   300
tactggtact tcgatctctg ggccgtggc accctggtca ccgtctctag t            351
```

<210> SEQ ID NO 10
<211> LENGTH: 117
<212> TYPE: PRT
<213> ORGANISM: Homo sapiens

<400> SEQUENCE: 10

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Ser Gly Ser Tyr Trp Tyr Phe Asp Leu Trp Gly Arg Gly Thr Leu
            100                 105                 110

Val Thr Val Ser Ser
        115
```

<210> SEQ ID NO 11
<211> LENGTH: 324
<212> TYPE: DNA
<213> ORGANISM: Homo Sapiens

<400> SEQUENCE: 11

```
gaaattgtgt tgacgcagtc tccaggcacc ctgtctttgt ctccagggga aagagccacc    60
ctctcctgca gggccagtca gagtgttagc agcagctcct tagcctggta ccagcagaaa   120
cctggccagg ctcccaggct cctcatatat ggtgcatcca gcagggccac tggcatccca   180
gacaggttca gtggcagtgg gtctgggaca gacttcactc tcaccatcag cagactggag   240
cctgaagatt ttgcagtgta ttactgtcag cggtctggtg gctcatcatt cactttcggc   300
cctgggacca aagtggatat caaa                                          324
```

<210> SEQ ID NO 12
<211> LENGTH: 108
<212> TYPE: PRT
<213> ORGANISM: Homo sapiens

<400> SEQUENCE: 12

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Ser Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Arg Ser Gly Gly Ser Ser
                85                  90                  95
Phe Thr Phe Gly Pro Gly Thr Lys Val Asp Ile Lys
            100                 105
```

<210> SEQ ID NO 13
<211> LENGTH: 351
<212> TYPE: DNA
<213> ORGANISM: Homo Sapiens

<400> SEQUENCE: 13

```
gaggtgcagc tggtgcagtc tggagcagag gtgaaaaagc ccggggagtc tctgaagatc      60
tcctgtaagg gttctggata caactttacc agctactgga tcggctgggt gcgccagatg     120
cccgggaaag gcctggagtt gatggggatc atctatcctg gtgactctga taccagatac     180
agcccgtcct tccaaggcca ggtcaccatc tcagccgaca agtccatcag caccgcctac     240
ctgcagtgga gcagcctgaa ggcctcggac accgccatgt attactgtgg ttcggggagc     300
tactggtact tcgatctctg gggccgtggc accctggtca ccgtctctag t              351
```

<210> SEQ ID NO 14
<211> LENGTH: 117
<212> TYPE: PRT
<213> ORGANISM: Homo sapiens

<400> SEQUENCE: 14

```
Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Asn Phe Thr Ser Tyr
            20                  25                  30
Trp Ile Gly Trp Val Arg Gln Met Pro Gly Lys Gly Leu Glu Leu Met
        35                  40                  45
Gly Ile Ile Tyr Pro Gly Asp Ser Asp Thr Arg Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Gly Ser Gly Ser Tyr Trp Tyr Phe Asp Leu Trp Gly Arg Gly Thr Leu
            100                 105                 110
Val Thr Val Ser Ser
115
```

<210> SEQ ID NO 15
<211> LENGTH: 324
<212> TYPE: DNA
<213> ORGANISM: Homo Sapiens

<400> SEQUENCE: 15

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatatat ggtgcatcca gcagggccac tggcatccca   180
gacaggttca gtggcagtgg gtctgggaca gacttcactc tcaccatcag cagactggag   240
cctgaagatt ttgcagtgta ttactgtcag cggtctggtg gctcatcatt cactttcggc   300
cctgggacca aagtggatat caaa                                          324
```

<210> SEQ ID NO 16
<211> LENGTH: 108
<212> TYPE: PRT
<213> ORGANISM: Homo sapiens

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Ser Gly Gly Ser Ser
                85                  90                  95

Phe Thr Phe Gly Pro Gly Thr Lys Val Asp Ile Lys
            100                 105

<210> SEQ ID NO 17
<211> LENGTH: 447
<212> TYPE: PRT
<213> ORGANISM: homo sapiens

<400> SEQUENCE: 17

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Ser Tyr
            20                  25                  30

Trp Ile Gly Trp Val Arg Gln Met Pro Gly Lys Gly Leu Glu Leu Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Thr Ala Tyr
65                  70                  75                  80

Leu Gln Trp Ser Ser Leu Lys Ala Ser Asp Thr Ala Met Tyr Tyr Cys
                85                  90                  95

Gly Ser Gly Ser Tyr Phe Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

-continued

```
Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 18
<211> LENGTH: 215
<212> TYPE: PRT
<213> ORGANISM: Homo sapiens

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60
```

-continued

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Arg Ser Gly Gly Ser Ser
                 85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 19
<211> LENGTH: 447
<212> TYPE: PRT
<213> ORGANISM: Homo sapiens

<400> SEQUENCE: 19

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
                 20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Gly Ser Gly Ser Tyr Trp Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220
```

```
Thr Cys Pro Pro Cys Pro Ala Pro Glu Leu Leu Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 20
<211> LENGTH: 215
<212> TYPE: PRT
<213> ORGANISM: Homo sapiens

<400> SEQUENCE: 20

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Ser Gly Gly Ser Ser
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160
```

```
Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 21
<211> LENGTH: 447
<212> TYPE: PRT
<213> ORGANISM: Homo sapiens

<400> SEQUENCE: 21

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Ser Gly Ser Tyr Trp Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 22
<211> LENGTH: 215
<212> TYPE: PRT
<213> ORGANISM: Homo sapiens

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Ser Gly Gly Ser Ser
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 23
<211> LENGTH: 24
<212> TYPE: DNA
<213> ORGANISM: artificial
```

```
<220> FEATURE:
<223> OTHER INFORMATION: oligunucleotide primer for PCR
<220> FEATURE:
<221> NAME/KEY: misc_feature
<222> LOCATION: (18)..(23)
<223> OTHER INFORMATION: n is a, c, t, or g

<400> SEQUENCE: 23
ggccggatag gcctccannn nnnt                                          24

<210> SEQ ID NO 24
<211> LENGTH: 21
<212> TYPE: DNA
<213> ORGANISM: artificial
<220> FEATURE:
<223> OTHER INFORMATION: olignucleotide primer for PCR

<400> SEQUENCE: 24
ggggtcaggc tggaactgag g                                             21

<210> SEQ ID NO 25
<211> LENGTH: 19
<212> TYPE: DNA
<213> ORGANISM: artificial
<220> FEATURE:
<223> OTHER INFORMATION: oligonucleotide primer for PCR

<400> SEQUENCE: 25
tgaggacgct gaccacacg                                                19

<210> SEQ ID NO 26
<211> LENGTH: 48
<212> TYPE: DNA
<213> ORGANISM: artificial
<220> FEATURE:
<223> OTHER INFORMATION: oligonucleotide primer for PCR

<400> SEQUENCE: 26
acaacaaagc ttctagacca ccatggaaac cccagctcag cttctctt                48

<210> SEQ ID NO 27
<211> LENGTH: 33
<212> TYPE: DNA
<213> ORGANISM: artificial
<220> FEATURE:
<223> OTHER INFORMATION: oligonucleotide primer for PCR

<400> SEQUENCE: 27
cttgtcgact caacactctc ccctgttgaa gct                                33

<210> SEQ ID NO 28
<211> LENGTH: 44
<212> TYPE: DNA
<213> ORGANISM: artificial
<220> FEATURE:
<223> OTHER INFORMATION: oligonucleotide primer for PCR

<400> SEQUENCE: 28
cagcagaagc ttctagacca ccatggggtc aaccgccatc ctcg                    44

<210> SEQ ID NO 29
<211> LENGTH: 42
<212> TYPE: DNA
<213> ORGANISM: artificial
<220> FEATURE:
<223> OTHER INFORMATION: oligonucleotide primer for PCR

<400> SEQUENCE: 29
```
cttggtggag gcactagaga cggtgaccag ggtgccacgg cc                42

<210> SEQ ID NO 30
<211> LENGTH: 117
<212> TYPE: PRT
<213> ORGANISM: homo sapiens

<400> SEQUENCE: 30

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Ser Gly Ser Tyr Trp Tyr Phe Asp Leu Arg Gly Arg Gly Thr Leu
            100                 105                 110

Val Thr Val Ser Ser
        115

<210> SEQ ID NO 31
<211> LENGTH: 109
<212> TYPE: PRT
<213> ORGANISM: homo sapiens

<400> SEQUENCE: 31

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ile Ser Ser
            20                  25                  30

Tyr Leu Ala Trp Tyr Gln Gln Lys Pro Gly Gln Thr Pro Arg Leu Leu
        35                  40                  45

Ile Tyr Gly Val Ser Ser Arg Ala Thr Gly Ile Pro Asp Arg Phe Ser
    50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Gly Asn Ser Phe
                85                  90                  95

Met Tyr Thr Phe Gly Gln Gly Thr Lys Leu Glu Ile Lys
            100                 105

<210> SEQ ID NO 32
<211> LENGTH: 447
<212> TYPE: PRT
<213> ORGANISM: Homo sapiens

<400> SEQUENCE: 32

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
            50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Ser Gly Ser Tyr Trp Tyr Phe Asp Leu Arg Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 33
<211> LENGTH: 216
<212> TYPE: PRT

<213> ORGANISM: Homo sapiens

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ile Ser Ser
            20                  25                  30

Tyr Leu Ala Trp Tyr Gln Gln Lys Pro Gly Gln Thr Pro Arg Leu Leu
        35                  40                  45

Ile Tyr Gly Val Ser Ser Arg Ala Thr Gly Ile Pro Asp Arg Phe Ser
    50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Gly Asn Ser Phe
                85                  90                  95

Met Tyr Thr Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 34
<211> LENGTH: 5
<212> TYPE: PRT
<213> ORGANISM: Homo sapiens

<400> SEQUENCE: 34

Ser Tyr Trp Ile Gly
1               5

<210> SEQ ID NO 35
<211> LENGTH: 17
<212> TYPE: PRT
<213> ORGANISM: Homo sapiens

<400> SEQUENCE: 35

Ile Ile Tyr Pro Gly Asp Ser Asp Thr Arg Tyr Ser Pro Ser Phe Gln
1               5                   10                  15

Gly

<210> SEQ ID NO 36
<211> LENGTH: 8
<212> TYPE: PRT
<213> ORGANISM: Homo sapiens

<400> SEQUENCE: 36

Gly Ser Tyr Phe Tyr Phe Asp Leu
1               5

```
<210> SEQ ID NO 37
<211> LENGTH: 8
<212> TYPE: PRT
<213> ORGANISM: Homo sapiens

<400> SEQUENCE: 37

Gly Ser Tyr Trp Tyr Phe Asp Leu
1               5

<210> SEQ ID NO 38
<211> LENGTH: 12
<212> TYPE: PRT
<213> ORGANISM: Homo sapiens

<400> SEQUENCE: 38

Arg Ala Ser Gln Ser Val Ser Ser Ser Tyr Leu Ala
1               5                   10

<210> SEQ ID NO 39
<211> LENGTH: 12
<212> TYPE: PRT
<213> ORGANISM: Homo sapiens

<400> SEQUENCE: 39

Arg Ala Ser Gln Ser Val Ser Ser Ser Leu Ala
1               5                   10

<210> SEQ ID NO 40
<211> LENGTH: 12
<212> TYPE: PRT
<213> ORGANISM: Homo sapiens

<400> SEQUENCE: 40

Arg Ala Ser Gln Ser Ile Ile Ser Ser Tyr Leu Ala
1               5                   10

<210> SEQ ID NO 41
<211> LENGTH: 7
<212> TYPE: PRT
<213> ORGANISM: Homo sapiens

<400> SEQUENCE: 41

Gly Ala Ser Ser Arg Ala Thr
1               5

<210> SEQ ID NO 42
<211> LENGTH: 7
<212> TYPE: PRT
<213> ORGANISM: Homo sapiens

<400> SEQUENCE: 42

Gly Val Ser Ser Arg Ala Thr
1               5

<210> SEQ ID NO 43
<211> LENGTH: 9
<212> TYPE: PRT
<213> ORGANISM: Homo sapiens

<400> SEQUENCE: 43

Gln Arg Ser Gly Gly Ser Ser Phe Thr
1               5

<210> SEQ ID NO 44
```

```
<211> LENGTH: 10
<212> TYPE: PRT
<213> ORGANISM: Homo sapiens

<400> SEQUENCE: 44

Gln Gln Tyr Gly Asn Ser Phe Met Tyr Thr
1               5                   10

<210> SEQ ID NO 45
<211> LENGTH: 24
<212> TYPE: DNA
<213> ORGANISM: Homo sapiens

<400> SEQUENCE: 45
gggagctact tttacttcga tctc                                              24

<210> SEQ ID NO 46
<211> LENGTH: 24
<212> TYPE: DNA
<213> ORGANISM: Homo sapiens

<400> SEQUENCE: 46
gggagctact ggtacttcga tctc                                              24

<210> SEQ ID NO 47
<211> LENGTH: 27
<212> TYPE: DNA
<213> ORGANISM: Homo sapiens

<400> SEQUENCE: 47
cagcggtctg gtggctcatc attcact                                           27

<210> SEQ ID NO 48
<211> LENGTH: 9
<212> TYPE: PRT
<213> ORGANISM: Homo sapiens
<220> FEATURE:
<221> NAME/KEY: UNSURE
<222> LOCATION: (2)..(9)
<223> OTHER INFORMATION: X is any amino acid

<400> SEQUENCE: 48

Cys Xaa Xaa Xaa Xaa Xaa Xaa Xaa Xaa
1               5

<210> SEQ ID NO 49
<211> LENGTH: 5
<212> TYPE: PRT
<213> ORGANISM: Homo sapiens

<400> SEQUENCE: 49

Leu Glu Trp Ile Gly
1               5

<210> SEQ ID NO 50
<211> LENGTH: 4
<212> TYPE: PRT
<213> ORGANISM: Homo sapiens
<220> FEATURE:
<221> NAME/KEY: UNSURE
<222> LOCATION: (3)..(3)
<223> OTHER INFORMATION: X is any amino acid

<400> SEQUENCE: 50

Trp Gly Xaa Gly
1
```

<210> SEQ ID NO 51
<211> LENGTH: 4
<212> TYPE: PRT
<213> ORGANISM: Homo sapiens
<220> FEATURE:
<221> NAME/KEY: UNSURE
<222> LOCATION: (3)..(3)
<223> OTHER INFORMATION: X is any amino acid

<400> SEQUENCE: 51

Phe Gly Xaa Gly
1

<210> SEQ ID NO 52
<211> LENGTH: 20
<212> TYPE: PRT
<213> ORGANISM: Homo sapiens

<400> SEQUENCE: 52

Met Glu Thr Asp Thr Leu Leu Leu Trp Val Leu Leu Leu Trp Val Pro
1               5                   10                  15

Gly Ser Thr Gly
            20

<210> SEQ ID NO 53
<211> LENGTH: 26
<212> TYPE: PRT
<213> ORGANISM: Homo sapiens

<400> SEQUENCE: 53

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 54
<211> LENGTH: 19
<212> TYPE: PRT
<213> ORGANISM: Homo sapiens

<400> SEQUENCE: 54

Met Gly Ser Thr Ala Ile Leu Ala Leu Leu Ala Val Leu Gln Gly
1               5                   10                  15

Val Cys Ala

<210> SEQ ID NO 55
<211> LENGTH: 20
<212> TYPE: PRT
<213> ORGANISM: Homo sapiens

<400> SEQUENCE: 55

Met Glu Thr Pro Ala Gln Leu Leu Phe Leu Leu Leu Leu Trp Leu Pro
1               5                   10                  15

Asp Thr Thr Gly
            20

<210> SEQ ID NO 56
<211> LENGTH: 351
<212> TYPE: DNA
<213> ORGANISM: Homo sapiens

<400> SEQUENCE: 56
gaggtgcagc tggtgcagtc tggagcagag gtgaaaaagc ccggggagtc tctgaagatc      60

```
                                    -continued
tcctgtaagg gttctggata cagctttacc agctactgga tcggctgggt gcgccagatg     120
cccgggaaag gcctggagtg gatggggatc atctatcctg gtgactctga taccagatac    180
agcccgtcct tccaaggcca ggtcaccatc tcagccgaca agtccatcag caccgcctac    240
ctgcagtgga gcagcctgaa ggcctcggac accgccatgt attactgtgg ttcgggagc     300 tactggtact tcgatctccg gggccgtggc accctggtca ccgtctctag t             351

<210> SEQ ID NO 57
<211> LENGTH: 327
<212> TYPE: DNA
<213> ORGANISM: Homo sapiens

<400> SEQUENCE: 57
gaaattgtgt tgacgcagtc tccaggcacc ctgtctttgt ctccagggga aagagccacc      60
ctctcctgca gggccagtca gagtattatc agcagctact tagcctggta ccagcagaaa    120
cctggccaga ctcccaggct cctcatctat ggtgtatcca gcagggccac tggcatccca    180
gacaggttca gtggcagtgg gtctgggaca gacttcactc tcaccatcac cagactggag    240
cctgaagatt ttgcagtgta ttactgtcag cagtatggta actcatttat gtacactttt    300
ggccagggga ccaagctgga gatcaaa                                         327
```